(12) United States Patent
McAllister et al.

(10) Patent No.: US 12,138,416 B2
(45) Date of Patent: Nov. 12, 2024

(54) DRUG DELIVERY DEVICES HAVING SEPARABLE MICRONEEDLES AND METHODS

(71) Applicant: Georgia Tech Research Corporation, Atlanta, GA (US)

(72) Inventors: Devin V. McAllister, Marietta, GA (US); Mark R. Prausnitz, Atlanta, GA (US); Sebastien Henry, Smyrna, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 222 days.

(21) Appl. No.: 17/184,140

(22) Filed: Feb. 24, 2021

(65) Prior Publication Data

US 2021/0196937 A1  Jul. 1, 2021

Related U.S. Application Data

(62) Division of application No. 15/566,748, filed as application No. PCT/US2016/028164 on Apr. 18, 2016, now Pat. No. 10,940,301.

(Continued)

(51) Int. Cl.
*A61M 37/00* (2006.01)

(52) U.S. Cl.
CPC . *A61M 37/0015* (2013.01); *A61M 2037/0007* (2013.01); *A61M 2037/0023* (2013.01);

(Continued)

(58) Field of Classification Search
CPC ...... A61M 37/0015; A61M 2037/0007; A61M 2037/0023; A61M 2037/0046; A61M 2037/0061; A61M 37/0069; A61M 37/00
See application file for complete search history.

(56) References Cited

U.S. PATENT DOCUMENTS

| 6,503,231 B1 | 1/2003 | Prausnitz et al. |
| 7,166,086 B2 | 1/2007 | Haider et al. |

(Continued)

FOREIGN PATENT DOCUMENTS

| CN | 104069585 A | 10/2014 |
| CN | 204017140 U | 12/2014 |

(Continued)

OTHER PUBLICATIONS

European Third Party Observation for EP Application No. 20180890093.0 mailed May 16, 2022 (4 pages).

(Continued)

*Primary Examiner* — James D Ponton
(74) *Attorney, Agent, or Firm* — Eversheds Sutherland (US) LLP

(57) ABSTRACT

Drug delivery devices and methods are provided for delivering one or more drugs into a biological tissue. The devices include microneedles that may be separable from the drug delivery devices, control drug release rate and/or direction, or a combination thereof. When the microneedles are separable, a force applied to the drug delivery devices may be effective to penetrate a biological tissue with the microneedles and then to separate the microneedles from the drug delivery devices. The drug delivery devices may be capable of achieving discrete periods of drug release. Methods for delivery drug with microneedles also are provided.

28 Claims, 7 Drawing Sheets

Related U.S. Application Data

(60) Provisional application No. 62/149,043, filed on Apr. 17, 2015.

(52) U.S. Cl.
CPC .............. *A61M 2037/0046* (2013.01); *A61M 2037/0061* (2013.01)

(56) References Cited

U.S. PATENT DOCUMENTS

| | | | |
|---|---|---|---|
| 8,075,826 | B2 | 12/2011 | Lastovich et al. |
| 8,708,966 | B2 | 4/2014 | Allen et al. |
| 8,945,482 | B2 | 2/2015 | Mitragotri et al. |
| 9,114,238 | B2 | 8/2015 | Singh et al. |
| 9,492,647 | B2 | 11/2016 | Stumber et al. |
| 9,549,746 | B2 | 1/2017 | Woolfson et al. |
| 9,848,853 | B2 | 12/2017 | Mitragotri et al. |
| 9,993,625 | B2 | 6/2018 | Roth et al. |
| 10,737,081 | B2 | 8/2020 | Jung et al. |
| 10,967,164 | B2 | 4/2021 | Park et al. |
| 2002/0082543 | A1* | 6/2002 | Park ............... A61M 37/0015 604/20 |
| 2004/0106904 | A1* | 6/2004 | Gonnelli ........... A61M 37/0015 604/173 |
| 2005/0065463 | A1 | 3/2005 | Tobinaga et al. |
| 2005/0137525 | A1 | 6/2005 | Wang et al. |
| 2005/0137531 | A1 | 6/2005 | Prausnitz et al. |
| 2007/0078414 | A1 | 4/2007 | McAllister et al. |
| 2007/0225676 | A1 | 9/2007 | Prausnitz et al. |
| 2007/0260201 | A1 | 11/2007 | Prausnitz et al. |
| 2008/0009825 | A1* | 1/2008 | Ringsred ........... A61M 37/0015 604/506 |
| 2008/0027384 | A1 | 1/2008 | Wang et al. |
| 2008/0167601 | A1 | 7/2008 | Laermer et al. |
| 2008/0213461 | A1* | 9/2008 | Gill ..................... A61K 9/0021 427/2.3 |
| 2008/0262416 | A1* | 10/2008 | Duan .................. A61K 9/0021 427/2.1 |
| 2008/0269666 | A1 | 10/2008 | Wang et al. |
| 2009/0017210 | A1* | 1/2009 | Andrianov ........... A61K 9/0021 118/712 |
| 2009/0041810 | A1 | 2/2009 | Andrianov et al. |
| 2009/0118672 | A1 | 5/2009 | Gonnelli et al. |
| 2009/0131905 | A1 | 5/2009 | Allen et al. |
| 2009/0182306 | A1 | 7/2009 | Lee et al. |
| 2009/0187160 | A1 | 7/2009 | McAllister et al. |
| 2009/0324374 | A1 | 12/2009 | De Carli |
| 2010/0256064 | A1* | 10/2010 | Woolfson ............. A61B 17/205 514/561 |
| 2012/0226260 | A1 | 9/2012 | Prausnitz et al. |
| 2013/0165902 | A1 | 6/2013 | Stumber et al. |
| 2013/0338596 | A1 | 12/2013 | McAllister |
| 2013/0338597 | A1 | 12/2013 | McAllister |
| 2014/0005606 | A1 | 1/2014 | Chen et al. |
| 2014/0180201 | A1 | 6/2014 | Ding et al. |
| 2014/0236089 | A1 | 8/2014 | Brouwers et al. |
| 2015/0057604 | A1 | 2/2015 | Arami et al. |
| 2015/0209180 | A1 | 7/2015 | Prausnitz et al. |
| 2016/0101272 | A1 | 4/2016 | McAllister |
| 2016/0107189 | A1 | 4/2016 | Hashimoto et al. |
| 2016/0213908 | A1 | 7/2016 | McAllister et al. |
| 2017/0050010 | A1 | 2/2017 | McAllister et al. |
| 2017/0273827 | A1 | 9/2017 | Prausnitz et al. |
| 2018/0078498 | A1 | 3/2018 | Petersson et al. |
| 2018/0133447 | A1 | 5/2018 | McAllister et al. |
| 2019/0001108 | A1 | 1/2019 | Ono |
| 2019/0015651 | A1 | 1/2019 | Tadros et al. |
| 2020/0238065 | A1 | 7/2020 | Prausnitz et al. |

FOREIGN PATENT DOCUMENTS

| | | |
|---|---|---|
| CN | 104338235 A | 2/2015 |
| EP | 1239917 B1 | 5/2005 |
| JP | 2010233674 A | 10/2010 |
| JP | 2012200572 A | 10/2012 |
| JP | 2017164191 A | 9/2017 |
| WO | 2008053481 A1 | 5/2008 |

OTHER PUBLICATIONS

Japanese Office Action Corresponding Japanese Patent Application No. 2017-554327 dated Feb. 21, 2020.

Office Action for Russian Patent Application No. 2017139266 dated Sep. 19, 2019.

International Search Report and Written Opinion for PCT/US2016/028164, dated Aug. 11, 2016 (13 pages).

Chinese Office Action from Corresponding Chinese Patent Application No. 2016800256937 dated Jan. 20, 2020.

Japanese Office Action Corresponding Japanese Patent Application No. 2017-554327 dated Aug. 28, 2020.

First Examination Report from corresponding Indian application 201717039205 dated Jan. 9, 2020. (5 pages).

Written Opinion of the International Search Authority, dated Jan. 7, 2019, for PCT/US2018/055519.

Li, et al., "Rapidly Separable Microneedle Patches for Sustained Release of Contraceptive Hormones," Abstract published by Biomedical Engineering Society, Apr. 24, 2017 (1 page).

Chu, et al., "Fabrication of Dissolving Polymer Microneedles for Controlled Drug Encapsulation and Delivery: Bubble and Pedestal Designs," J. Pharmaceutical Sciences, 99(10): 4228-38 (Oct. 2010).

Wang, et al., "Microneedles with Controlled Bubble Sizes and Drug Distributions for Efficient Transdermal Drug Delivery," Scientific Reports, 6:38755, DOI:10.1038/srep38755 (Dec. 2016).

* cited by examiner

DRUG DELIVERY DEVICES HAVING SEPARABLE MICRONEEDLES AND METHODS

CROSS-REFERENCE TO RELATED APPLICATIONS

This application is a divisional of U.S. application Ser. No. 15/566,748, filed Oct. 16, 2017, which is national stage of International Application No. PCT/US2016/028164, filed Apr. 18, 2016, which claims priority to U.S. Provisional Patent Application No. 62/149,043, filed Apr. 17, 2015, all of which are incorporated herein by reference.

STATEMENT REGARDING FEDERALLY SPONSORED RESEARCH

This invention was made with Government support under Contract Number EB012495 awarded by the National Institutes of Health. The Government has certain rights in the invention.

BACKGROUND

The present application is generally in the field of microneedles for the transport of therapeutic, diagnostic, cosmetic, biological or other molecules into, out of or across biological tissues, including the skin.

Microneedles are small in size, which allows them to target tissue layers, and to be relatively pain free in doing so. However, their small size typically requires associating the microneedles with a substrate or other structure to facilitate handling during production and application to (i.e., insertion of the microneedles into) biological tissue. Therefore, after application, the substrate or other structure (e.g., a patch) may need to remain on the tissue surface after microneedle insertion and during the period of release of the drug or other agent, which may be disadvantageous.

A substrate or other structure, following penetration of a biological tissue with microneedles, can be uncomfortable and/or inconvenient for a patient and/or subject to external forces that undesirably change the location or characteristics of the microneedles. Moreover, current substrates and other structures associated with microneedles do not provide a convenient and/or reliable and quick way to separate the microneedles from the substrates or other structures.

Microneedles, due to their size, are capable of targeting specific tissue layers and providing controlled release of drug into those tissues. It would be desirable to provide additional techniques of managing release kinetics in order to increase the types and ranges of release profiles that can be provided. For example, although certain matrix materials are known to release drugs at a particular rate, current microneedle configurations lack the ability to "turn off" or substantially increase or decrease drug release rate at a desired time after deployment. Conventional configurations also may not provide a mechanism for directing the direction of diffusion of drug release and/or may not control the region of the microneedles from which drug is released.

There remain needs to improve drug delivery device designs for better insertion and separation of microneedles, and/or control of drug release rate and location.

SUMMARY

Improved drug delivery devices and methods of drug delivery have been developed which address one or more of the above-described needs.

In one aspect, a drug delivery device for delivering a drug with separable microneedles is provided. In one embodiment, the drug delivery device with separable microneedles includes a substrate having a microneedle side and an opposing back side, an array of microneedles extending from the microneedle side of the substrate, wherein the microneedles comprise a drug, a supporting layer arranged on the opposing back side of the substrate, and at least one feature configured to separate the array of microneedles from the substrate upon application of a force to the substrate sufficient to at least partially penetrate a tissue surface with the array of microneedles.

In another embodiment, the drug delivery device having separable microneedles includes a housing having a depressible portion, a substrate having a microneedle side and an opposing back side, an array of microneedles extending from the microneedle side of the substrate, wherein the microneedles comprise a drug, and a supporting layer arranged on the opposing back side of the substrate, and movably mounted within the housing, wherein the depressible portion is configured to apply or activate upon depression a shearing force to at least one of the supporting layer and substrate effective to separate the array of microneedles from the substrate. The shearing force, in embodiments, is a rotational or linear/lateral shearing force. The drug delivery device may also include an apparatus that applies a shearing force upon depression of the depressible portion.

In one aspect, a method of inserting microneedles into a biological tissue for administering a drug into the biological tissue is provided. In embodiments, the methods include positioning a drug delivery device on the biological tissue surface, the drug delivery device comprising an array of microneedles, which comprise the drug, extending from a substrate, and applying a force to the device effective to (i) penetrate the tissue surface with the array of microneedles, and (ii) separate the array of microneedles from the substrate. The positioning and applying steps may individually or both be performed manually. In one embodiment, penetration of the tissue surface and separation of the array of microneedles from the substrate occur substantially simultaneously.

In another aspect, a drug delivery device is provided that is capable of controlling the rate and/or direction of drug release. In one embodiment, the drug delivery device includes an array of microneedles which comprise a drug and which extend from a base, and a system for triggering, after the microneedles are inserted at least partially into a biological tissue, a change in rate of release of the drug from the microneedles and into the biological tissue. In another embodiment, the drug delivery device includes a substrate having a microneedle side and an opposing back side, an array of microneedles extending from the microneedle side of the substrate, wherein the microneedles comprise a drug, a supporting layer arranged on the opposing back side of the substrate, and a barrier configured to permit (i) discrete periods of drug release upon or after implantation, (ii) control of the region of the microneedles from which the drug is released, or (iii) a combination thereof. In a further embodiment, the drug delivery devices include a barrier that is capable of controlling drug release rate and/or location of drug release.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
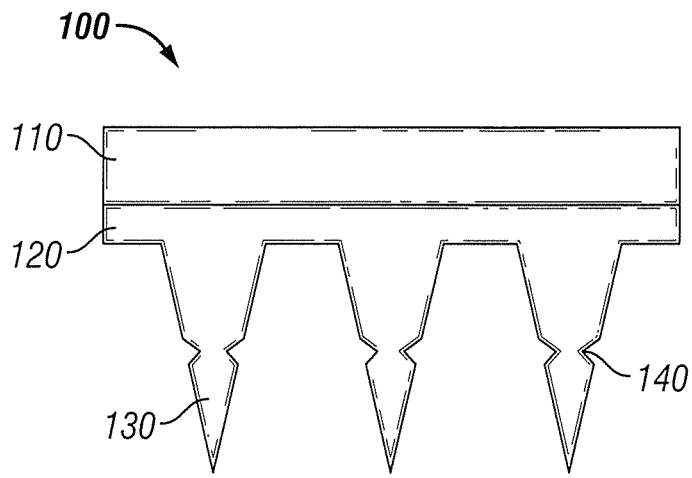
FIG. 1A depicts, in a cross-sectional view, one embodiment of a drug delivery device having an array of microneedles, in which the microneedles include an example of a predefined fracture region.

Improved drug delivery devices and methods of inserting microneedles have been developed. In embodiments, the drug delivery devices include an array of microneedles extending from a substrate, and at least one feature configured to separate the array of microneedles from the substrate upon application of a force to the substrate. The force applied to the substrate may be effective to at least partially penetrate a biological tissue with the array of microneedles. To clarify, an input force leads to two different forces being applied to the microneedles. A first force has the effect primarily of inserting the microneedles into the tissue, and a second force has the effect primarily of separating the microneedles from the substrate.

In embodiments, one or more microneedles of the array of microneedles advantageously separate from the substrate upon application of a force effective to at least partially penetrate a tissue surface with the array of microneedles. Therefore, in some embodiments, the application of a force is effective to [1] penetrate a biological tissue with the array of microneedles, and then [2] separate one or more microneedles of the array of microneedles from the substrate. The separated microneedles may then remain at least partially embedded in the biological tissue. The substrate and remainder of the device beneficially may be removed from the tissue surface upon separation of the microneedles.

In a preferred embodiment, the tissue penetration and separation of the microneedles occur sequentially but nearly simultaneously. In this way, for example, a user can manually apply the device against a person's skin, and simply depress a button or other portion of the device, or twist the device, to both insert the microneedles into the skin and separate the microneedles from the device, in a simple and quick motion. This advantageously simplifies the administration process and avoids the need to have some external device portion remain on the skin surface for a prolonged period, e.g., during drug release or while waiting for a dissolution-driven separation to occur.

As used herein, the term "user" in reference to use of the devices described here may be a person to whom the microneedles are administered (i.e., when self-administered) or may be a person who administers the microneedles to another person or animal. For example, the user may be a doctor or nurse or other medical professional who applies the microneedle device to a patient in need of a drug for treatment or prophylaxis.

In embodiments of the devices and their use described herein, there is a discontinuity in a force-displacement curve—i.e., the input force (i.e., the force applied by the user to the device) leads to a displacement of the microneedles. In one case, a continuous input force leads to a non-continuous microneedle displacement. For example, the output force (i.e., the force applied to the microneedles or the substrate) initially moves the microneedles in the perpendicular direction (toward/into the target tissue site) and then suddenly shifts movement to the lateral direction. In an alternative example, the shift from perpendicular to lateral movement happens continuously.

An important aspect of the devices and methods described herein is that the separation of the microneedles from the substrate occurs during application of the input force by a user. In contrast, a conventional system describes separation to occur based on a dissolution process that occurs after microneedle insertion and after no more force is applied to the microneedle device. In such conventional cases, at some later time (e.g., several minutes or hours), the microneedles (or a portion of the microneedles) get wet and soft and may form a gel and partially dissolve such that the substrate can be removed from the tissue, and the microneedles stay behind in the tissue. Again in contrast, with the devices and methods described herein separation of the microneedles advantageously is not facilitated (at all or substantially) by interaction of the microneedles with water in the tissue or imbibing water or dissolving or any other such process.

A further advantage of the presently disclosed devices and methods is that separation of the microneedles does not depend on the microneedle having some sort of barb feature to resist withdrawal of the microneedle from the biological tissue, unlike some conventional systems. The microneedles of present disclosure therefore may have substantially smooth or straight sidewalls.

In some embodiments, a physical force, such as a shear force, is applied to the microneedles that causes them to break. In other embodiments, there is a change in mechanical properties of the microneedles and/or the substrate that causes their separation, i.e., the microneedle interface with the substrate is made weaker, which leads to separation, due to less shear or even without any shear. For example, a predefined fracture region may be formed of or include one or more anisotropic materials or composites. In some embodiments, there is a trigger that can change the mechanical properties of the microneedles upon insertion into skin or other biological tissue. Examples of these triggers include (i) pressure due to the force of insertion causing a phase change (e.g., solid to liquid phase change, from one crystal structure to another crystal structure) that facilitates the microneedle separation; (ii) liquid contacting the microneedle interface and dissolving it or otherwise weakening it, wherein the force of insertion initiates release of a liquid stored in the device and that liquid dissolves/weakens the microneedle interface; and (iii) pressing the device to insert the microneedles into the biological tissue completes (or disconnects) an electrical circuit that triggers a switch to mechanically break the microneedles or that changes a material property in the microneedles (e.g., alignment of charged molecules) due to the electric field that in turn leads to failure of a fracturable region of the device.

In some embodiments, the user's application of force downward against the device toward the biological tissue applies a force normal to the substrate to cause the separation of the microneedles from the substrate. For example, the force may cause the proximal end portion of the microneedles to be pushed through the substrate, fracturing it. In other embodiments, the user's application of force downward against the device toward the biological tissue applies a force parallel to the substrate to cause the separation of the microneedles from the substrate. For example, the parallel force may be linear or rotational.

Figure 1B:
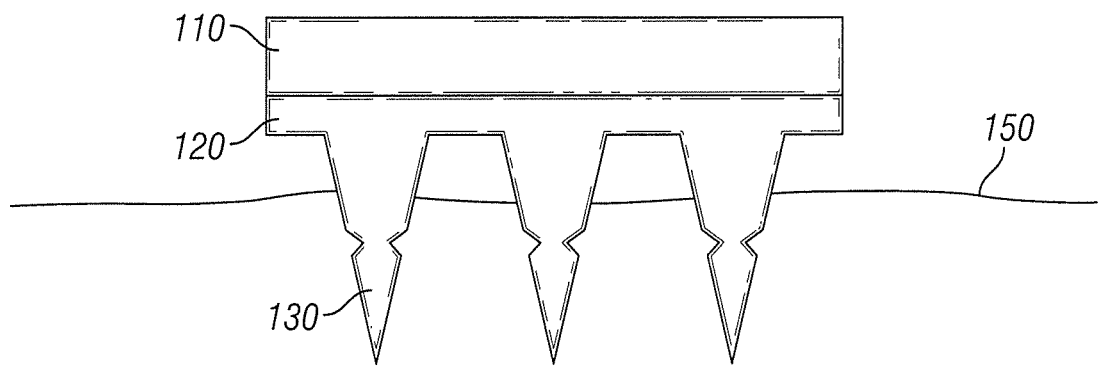
FIG. 1B depicts, in a cross-sectional view, one embodiment of a drug delivery device having an array of microneedles, in which a portion of the microneedles has penetrated a biological tissue surface.

One embodiment of a drug delivery device is depicted at FIG. 1A. The drug delivery device 100 includes a supporting layer 110 and a substrate 120 from which an array of microneedles 130 extends. The microneedles 130 of the drug delivery device 100 penetrate a tissue surface 150 (FIG. 1B), which results in fractured microneedles 160 (FIG. 1C), upon the application of a force. The microneedles of FIG. 1A include a predefined fracture region 140, but the presence of the predefined fracture region 140 is not required.

Improved drug delivery devices capable of controlling drug release and methods also are provided. In embodiments, the drug delivery devices include an array of microneedles which comprise a drug and which extend from a base; and a system for triggering, after the microneedles are inserted at least partially into a biological tissue, a change in rate of release of the drug from the microneedles and into the biological tissue. The system for triggering may change a drug release rate in response to a condition or a change in a condition, such as temperature, pH, pressure, etc. In one embodiment, the system for triggering comprises a barrier material positioned in or on at least part of the microneedle to impede release of the drug from the microneedle in at least one direction and/or for a predetermined period of time. The barrier material, for example, may encapsulate, completely or partially, all or a portion of a drug of the microneedles, coat at least a portion of the microneedles, or a combination thereof. The triggering changes may fall into one of three categories: (I) the triggering change may be due to an endogenous change within the tissue environment that was not the result of human intervention (e.g., an analyte concentration changes); (II) the triggering change may be due to human intervention, such as providing an electric field or applying pressure, or (III) the triggering change maybe due to a change within the microneedles without human intervention, such as a dissolution process working like a fuse that, once sufficient dissolution occurs, drug can be released that was previously entrapped.

In embodiments, the drug delivery devices include microneedles that separate upon application of a force to the devices, and a system for triggering a change in rate and/or location of release of the drug from the microneedles. In a preferred embodiment, the microneedle includes a barrier over the microneedle such that release of drug occurs only from the end portion/region where the separation occurs. In this way, delivery/release of drug occurs preferentially or exclusively to the tissue near to the end portion/region where the separation occurs. In the case of skin, the microneedle could separate from the substrate near the dermal-epidermal junction. That way, the part of the microneedle in the dermis would be coated and not release drug, but the top of the microneedle (where it separated) would release drug into the epidermis, which is often the site of skin disease.

Unless otherwise defined herein or below in the remainder of the specification, all technical and scientific terms used herein have meanings commonly understood by those of ordinary skill in the art to which the present disclosure belongs. It is also to be understood that the terminology used herein is for the purpose of describing particular embodiments only, and is not intended to be limiting. In describing and claiming the present embodiments, the following terminology will be used in accordance with the definitions set out below.

As used in this specification and the appended claims, the singular forms "a," "an," and "the" include plural referents unless the content clearly dictates otherwise. Thus, for example, reference to "a barrier material" can include a combination of two or more components; reference to "a predefined fracture region" can include two different predefined fracture regions, and the like. The term "about", as used herein, indicates the value of a given quantity can include quantities ranging within 10% of the stated value, or optionally within 5% of the value, or in some embodiments within 1% of the value.

Array of Microneedles

The microneedle arrays include two or more microneedles which extend from a surface of a base substrate. The phrase "base substrate" and the term "substrate" are used interchangeably herein. Each microneedle has a proximal end attached to the base substrate directly, or indirectly via one or more predefined fracture regions, and a distal tip end which is sharp and effective to penetrate biological tissue. The microneedle may have tapered sidewalls between the proximal and distal ends.

The length of a microneedle ($L_{MN}$) may be between about 50 μm and 2 mm. In most cases they are between about 200 μm and 1200 μm, and ideally between about 500 μm and 1000 μm. The volume of a microneedle ($V_{MN}$) can be between about 1 nl and 100 nl. In most cases, it is between about 5 nl and 20 nl.

In one embodiment, the array of microneedles includes from 10 to 1000 microneedles.

In a preferred embodiment, the microneedles are solid microneedles that include a substance of interest, such as an active pharmaceutical ingredient (API), which becomes solubilized in vivo following insertion of the microneedle into a biological tissue, e.g., into the skin of a patient. For example, the substance of interest may be mixed into a water soluble matrix material forming a solid microneedle. The substance of interest may be provided in a formulation which is bioerodible. As used herein, the term "bioerodible" means that the structure/material degrades in vivo by dissolution, enzymatic bond cleavage, hydrolysis, erosion, resorption, or a combination thereof. In a preferred embodiment, the substance of interest and a matrix material in which the substance of interest is dispersed form the structure of the microneedle. In a preferred embodiment, the matrix material of the bioerodible microneedle is water soluble, such that the entire microneedle dissolves in vivo. In another embodiment, the matrix material of the bioerodible microneedle is biodegradable, such that the microneedles are not soluble in the form originally inserted into the biological tissue, but undergo a chemical change in the body (e.g., break chemical bonds of a polymer) that renders the products of the chemical change (e.g., monomers or oligomers of the polymer) water soluble or otherwise clearable from the body.

In one embodiment, the microneedles within a given array of microneedles all contain the same active and excipients. However, the actives and/or the excipients may be different in each microneedle, in different rows of microneedles, or sections/regions of the microneedle array. Possible reasons for designing the microneedles with such segregation are: i) the different actives are incompatible with one another, ii) the different actives require different stabilizing excipients, and iii) different release profiles (e.g., combination of rapid bolus followed by a sustained release) are desired of a single active or of different actives.

The array of microneedles also includes a drug, active ingredient or agent, or substance of interest. The terms and phrases "drug," "active ingredient," "active agent," "active(s)," and "substance of interest" are used interchangeably herein. The drug may be inside and/or on the surface of the microneedles, inside and/or on the substrate, or a combination thereof. The drug may be dispersed in a particular region of the microneedles, disposed in one or more reservoirs within the microneedles, disposed in an area of high concentration, or a combination thereof.

Predefined Fracture Region

In embodiments, the drug delivery devices include a predefined fracture region. The substrate and/or one or more microneedles may include the predefined fracture region. In embodiments, this region may be considered to be a frangible interface between the microneedles and the substrate. The predefined fracture region may increase the likelihood that the microneedles or the microneedles and a portion of the substrate separate at or near a desired location. The predefined fracture region, in some embodiments, ensures that the microneedles or the microneedles and a portion of the substrate separate at or near a desired location.

In one embodiment, the substrate includes a predefined fracture region about each of the one or more microneedles of the array of microneedles. For example, the substrate may include predefined fracture regions configured to fracture as a force is applied to the device. The predefined fracture regions may fracture as a force is applied, typically after the microneedles are at least partially pushed into the substrate. The substrate, upon breakage of the predefined fracture region, may be rendered incapable of retaining the array of microneedles. In some embodiments, part of the substrate may be associated with the one or more microneedles upon separation and/or part of the one or more microneedles may be associated with the substrate upon separation.

In one embodiment, one or more microneedles of the array of microneedles include a predefined fracture region. The predefined fracture region may be located at a proximal end of one or more microneedles of the array of microneedles.

In one embodiment, one or more predefined fracture regions are included in the substrate and one or more microneedles of the array of microneedles.

In embodiments, the predefined fracture region comprises a structural or physical feature (i.e., a geometric feature) that increases the likelihood that the separation of the one or more microneedles will occur at a desired location, for example, where the force required to separate the microneedle from the substrate is greater in the perpendicular direction and less in the lateral direction. For example, the predefined fraction region may include a substantially narrowed portion, a scored portion, a notched portion, an interface of different materials, or a combination thereof. An interface of different materials may be provided by forming at least a portion of the substrate and at least a portion of the one or more microneedles from different materials or combinations of materials.

In other embodiments, the predefined fracture region is defined/controlled based on material properties (rather than geometric features), such that the material is stronger under compression and weaker under shear. That is, the predefined fracture region may be made of one or more materials with anisotropic mechanical properties. This might be achieved using a single material and might be achieved using composite materials using methods known in the art.

In one embodiment, each microneedle includes a predefined fracture region at its proximal end portion where it meets with a funnel portion that connects the microneedle to the base.

A single microneedle array may include two or more predefined fracture regions. For example, an array could include one row of microneedles having predefined fracture regions of a first type and a second row of microneedles having predefined fracture regions of a second type. For example, the differences could be beneficially designed for delivering two different substances of interest.

Figure 1C:
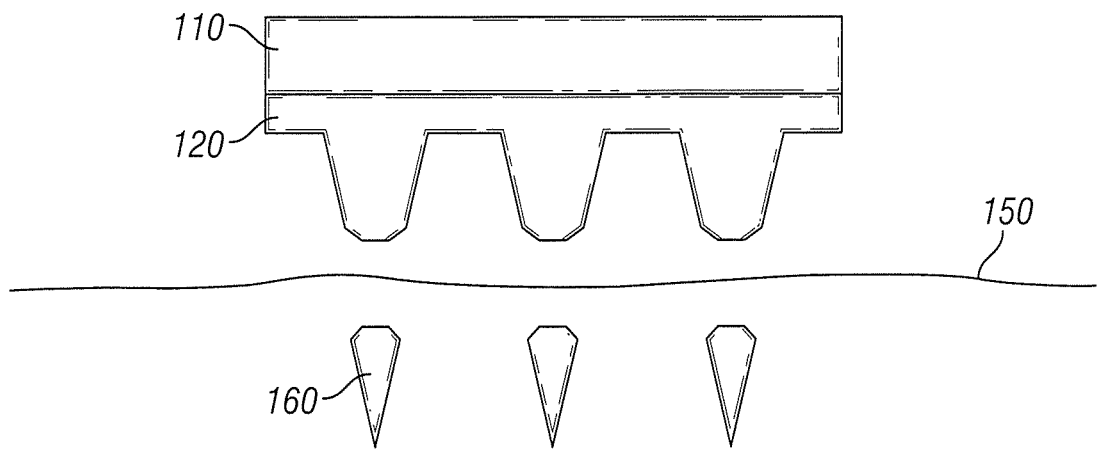
FIG. 1C depicts, in a cross-sectional view, one embodiment of a drug delivery device in which a predefined fracture region has fractured, separating microneedles from their substrate after the microneedles have been inserted into a biological tissue.

One embodiment of a predefined fracture region is depicted at FIG. 1A. The drug delivery device 100 of FIG. 1A includes a supporting layer 110 and a substrate 120 from which an array of microneedles 130 extend. Each of the microneedles 130 includes a notch 140, which facilitates separation of the portion of the microneedles 160 below the notches 140, as shown at FIG. 1C.

Figure 2A:
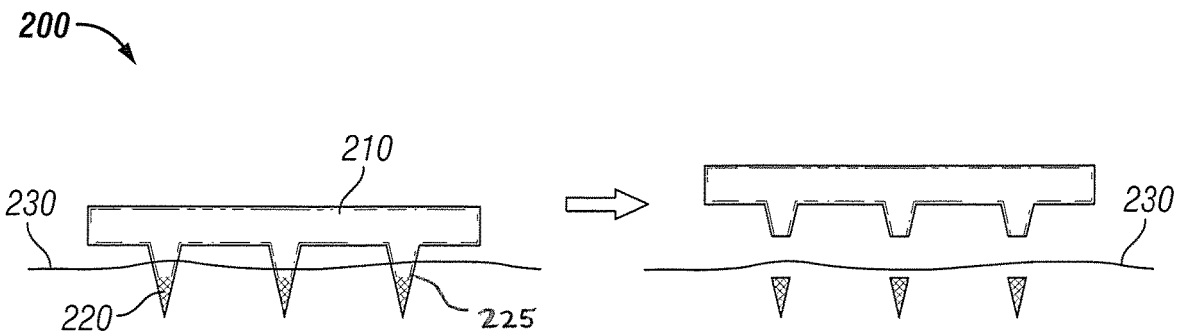
FIG. 2A depicts, in a cross-sectional view, one embodiment of a drug delivery device, and the separation of microneedles having one example of a predefined fracture region.

One embodiment of a predefined fracture region is depicted at FIG. 2A. The device 200 includes a substrate 210 and an array of microneedles 220 extending therefrom. The microneedles 220 and substrate 210 are formed of different materials, and the interface of these different materials 225 is a predefined fracture region. The microneedles 220 separate from the substrate 210 at the interface of the different materials 225 upon or after application of a force effective to penetrate the tissue surface 230 with the microneedles 220.

Figure 2B:
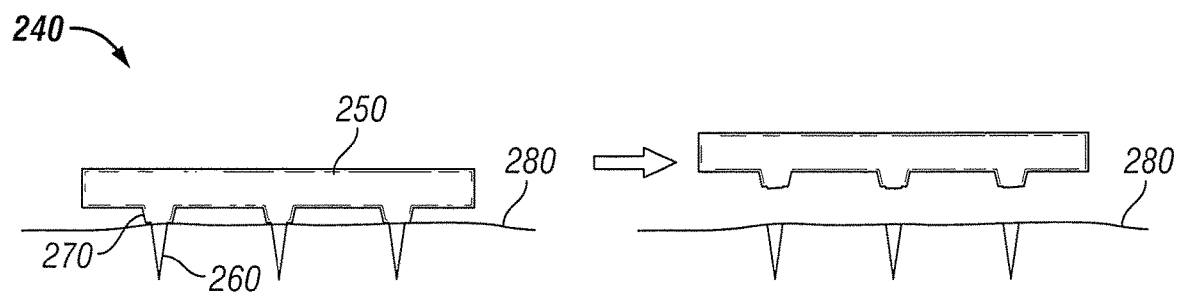
FIG. 2B depicts, in a cross-sectional view, one embodiment of a drug delivery device, and the separation of microneedles having another example of a predefined fracture region.

Another embodiment of a predefined fracture region is depicted at FIG. 2B. The device 240 includes a substrate 250 from which an array of microneedles extend. The microneedles include a funnel portion 270 and a substantially narrowed portion 260, which ensures that narrowed portion 260 of the microneedles separates from the substrate 250 upon or after application of a force effective to penetrate the tissue surface 280.

In still another embodiment, the separation of the microneedles from the substrate includes a buckling mode of failure. In one case, the interface between the substrate and microneedles includes columns connecting them with an open space between the columns. Then, application of purely perpendicular force to the columns causes the columns to buckle, which breaks them. When a column buckles, there is a lateral force that buckles the column materials laterally, such that a translation of perpendicular to lateral force occurs within the column. Accordingly, it is to understood that in some embodiments, such as described in the embodiments of FIGS. 4 and 5, the translation of a perpendicular to lateral force happens at a stage in the force transfer process before the substrate-microneedle interface, while in other embodiments, such as with the columns embodiment, the force translation occurs at the interface between the substrate and the microneedles.

Biological Tissue

The phrase "biological tissue," as used herein, generally includes any human or mammalian tissue. The biological tissue may be the skin or a mucosal tissue of a human or other mammal in need of treatment or prophylaxis. It is envisioned that the present devices and methods may also be adapted to other biological tissues and other animals.

The phrase "penetrate a tissue surface," as used herein, includes penetrating a biological tissue surface with any portion of one or more microneedles. Upon separation of a microneedle from a substrate, a proximal end of a microneedle may be above a tissue surface, substantially level with a tissue surface, or below a tissue surface.

Figure 3A:
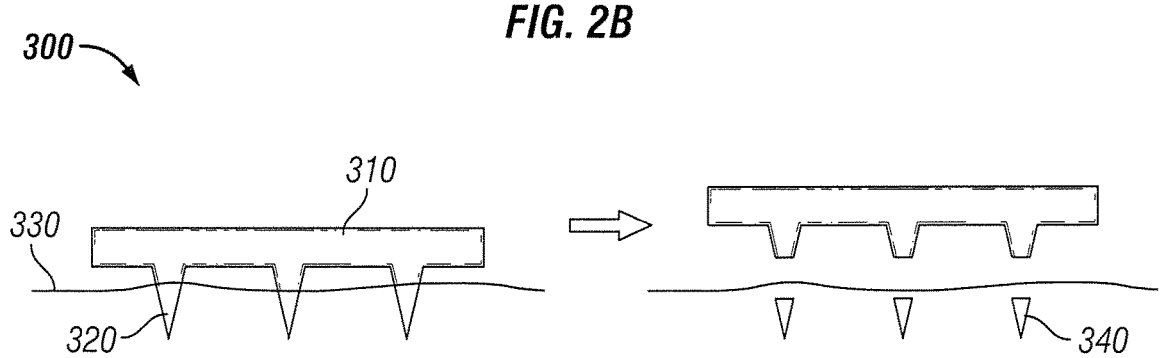
FIG. 3A depicts, in a cross-sectional view, one embodiment of a drug delivery device, and separated microneedles beneath a biological tissue surface.
Figure 3B:
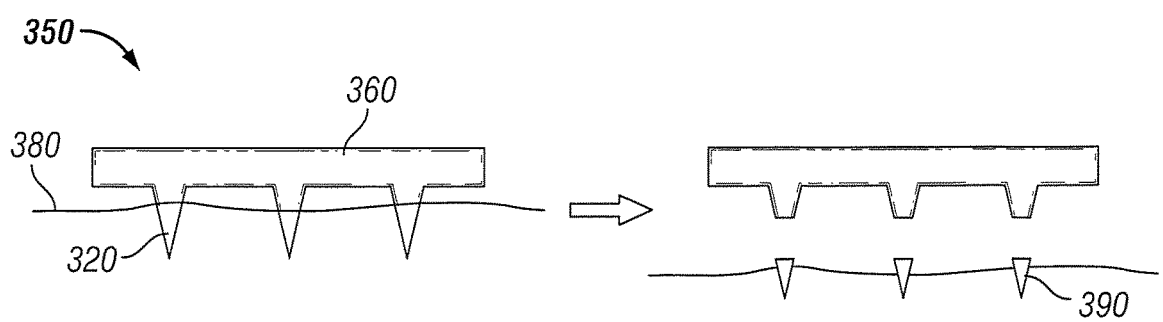
FIG. 3B depicts, in a cross-sectional view, one embodiment of a drug delivery device, and separated microneedles partially embedded in a biological tissue.

For example, FIG. 3A depicts one embodiment of a device 300 including a substrate 310 and microneedles 320 that have penetrated a biological tissue surface 330. Upon separation of the microneedles 320 from the substrate 310, the separated microneedles 340 are located entirely beneath the tissue surface 330. As a further example, FIG. 3B depicts another embodiment of a device 350 including a substrate 360 and microneedles 320 that have penetrated a biological tissue surface 380. Upon separation of the microneedles 320 from the substrate 360, a distal portion of the separated microneedles 390 is located beneath the tissue surface 380 and a proximal portion extends from the tissue surface. In other words, the separated microneedles 390 are partially embedded in the biological tissue.

In an alternative embodiment, the biological tissue is a plant tissue.

Force

In embodiments, the drug delivery devices provided herein are configured to respond advantageously to a force applied to the drug delivery devices. The force, in one embodiment, is effective to penetrate a biological tissue surface with one or more microneedles of an array of microneedles. The force, in another embodiment, is effective to penetrate a biological tissue surface with one or more microneedles of an array of microneedles, and separate one or more microneedles of the array of microneedles from the substrate.

In one embodiment, penetration of a biological tissue surface with the microneedles of an array of microneedles upon application of a force precedes the separation of the microneedles from the substrate. In another embodiment, penetration of a biological tissue surface with the microneedles of an array of microneedles, and separation of the microneedles from the substrate occur sequentially but substantially simultaneously upon application of a force. As used herein, the phrase "substantially simultaneously" refers to events that occur within 5 seconds, 3 seconds, 1 second, or less, of each other. In a preferred embodiment, the insertion and separation occur in a continuous motion by the user. In other words, a continuous force is applied by the user, during which the microneedles penetrate into the tissue and then at some point after penetration they break off. Even though forces applied to the microneedles may be discontinuous in direction during this process (e.g., perpendicular and then lateral to the tissue surface), the force applied by the use is substantially continuous in direction (e.g., perpendicular to the tissue surface). Often with this embodiment, the perpendicular movement (i.e., normal toward the surface of the biological tissue) of the microneedles has substantially stopped by the time the microneedle separation occurs, such that insertion and separation are sequential events.

One way to consider these embodiments is that one input from the user leads to two outputs from the device. The user presses in a continuous manner for a period of time. During this period, the device inserts the microneedles into the tissue and breaks them off in the tissue. The force application to the device is monophasic. The force output from the device is biphasic. It is also possible that the change in force direction is not biphasic but involves a continuous switch in direction of the force; for example, the force is initially perpendicular and then over time shifts its angle from about 90 degrees progressively to about 0 degrees and ends in a substantially lateral direction.

In one preferred embodiment, the force may be manually applied by a user. The device may transfer the force directly or indirectly to the predefined fracture region. The device may redirect the manually applied force, for example converting the downward force exerted by a user depressing a portion of the device (which is effective to cause the microneedles to penetrate the biological tissue) into a lateral or rotational force effective to fracture the predefined fracture region. In another preferred embodiment, the force may be a combination of a manual force and a released mechanical force stored in a spring or other component in the device.

In another preferred embodiment, the force may be applied manually by depressing a portion of the device, which imparts strain energy to the device that is stored briefly, for seconds or less, and is then released as rotational or horizontal shear thereby shearing off the microneedles. This can be achieved by converting the downward force by a rotating screw mechanism that temporarily stores the strain energy in a torsion spring. Once the desired force (controlled by loading/cocking the torsion spring) is applied (i.e., enough for the microneedles to either partially or completely insert into tissue), a latch releases this rotational energy onto the substrate thereby shearing the microneedles off the substrate and leaving them embedded in the tissue.

Generally, the input force may be applied to the device by a user on any vector or at any angle effective to achieve penetration, separation, or a combination thereof. In one embodiment, the input force is a substantially perpendicular force relative to the substrate. The output force applied to the microneedles, i.e., the force causing separation may be on the same vector or a different vector from the input force.

In embodiments, the input force, which typically would be applied to the device housing, imparts an output shearing force to the microneedles and/or substrate effective to separate one or more microneedles from an array of microneedles. The input force may impart a shearing force by applying a shearing force to the substrate, by activating an element that applies a shearing force to the substrate, or a combination thereof. In one case, the input force is substantially mono-directional, and the output force is at least bi-directional. In one embodiment, the shearing force is a rotational shearing force. In another embodiment, the shearing force is a lateral force.

Generally, the force may be applied to any portion of the drug delivery devices provided herein. The force, for example, may be applied directly to a substrate, supporting layer, or other portions of the devices described herein.

Housing

In embodiments, the drug delivery devices provided herein include a housing. At least one of the substrate and supporting layer may be associated with the housing in any manner. For example, at least one of the substrate or supporting layer may be disposed in the housing. As a further example, at least one of the substrate and supporting layer may be fixably or movably mounted in or on the housing by any means known in the art. For example, the substrate and/or supporting layer, when movably mounted, may be mounted on tracks, a central axis, or a combination thereof.

The housing may include a portion configured to accommodate the application of a force. In one embodiment, the portion configured to accommodate the application of a force is a depressible portion. The depressible portion generally may be any portion of the housing configured to transfer a force applied to the device to the substrate. For example, the depressible portion may include a piston-like apparatus movably mounted in the housing. In another example, the depressible portion may include an elastic portion of the housing that is depressible upon application of a force. The depressible portion may or may not contact the supporting layer and/or substrate prior to application of a force.

The depressible portion, in embodiments, imparts a shearing force to the substrate upon application of an input force. In some embodiments, the input force could be applied directly to the supporting layer which in turn imparts an output force to the substrate.

The depressible portion, in embodiments, applies a shearing force to the supporting layer and/or substrate by directly contacting the supporting layer and/or substrate. In one embodiment, at least a portion of the depressible portion that contacts the supporting layer and/or substrate is configured to impart motion to the supporting layer and/or substrate upon contact. In another embodiment, at least a portion of the depressible portion that contacts the supporting layer and/or substrate, and at least a portion of the supporting layer and/or substrate that contacts the depressible portion is configured to impart motion to the supporting layer and/or substrate. The contacting portions of the depressible portion, substrate, supporting layer, or a combination thereof may be angled, non-linear, etc., and the contacting surfaces may be lubricated and/or coated or constructed with a material that promotes the motion of the supporting layer and/or substrate.

Figure 4:
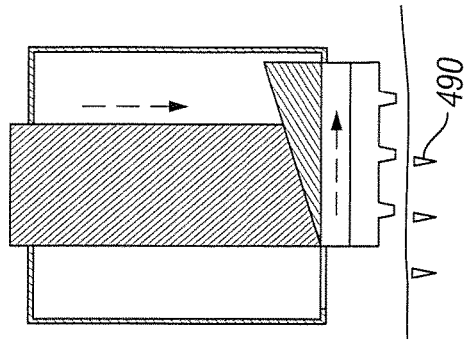
FIG. 4 depicts, in side and cross-sectional views, one embodiment of a drug delivery device having a depressible portion capable of imparting a lateral shearing force to separate microneedles that have been inserted into a biological tissue.
Figure 4:
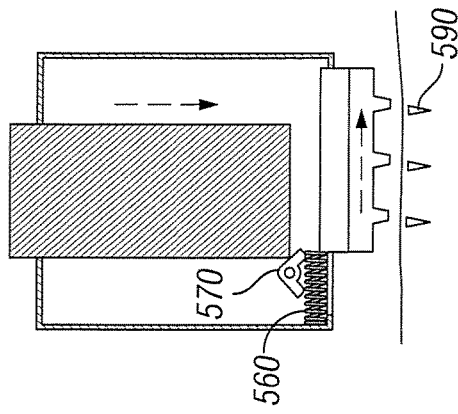
Figure 4:
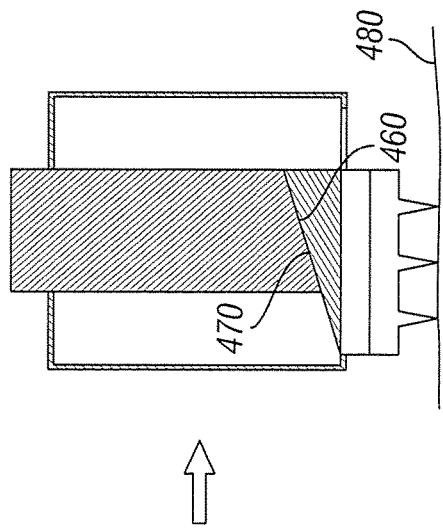
Figure 4:
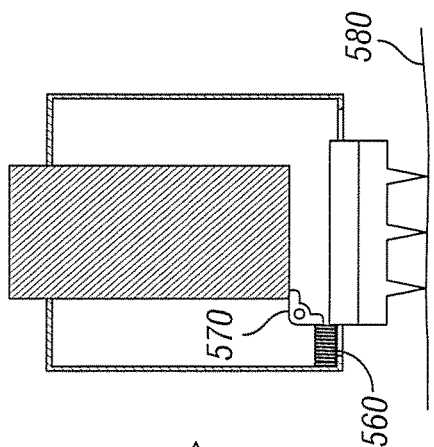
Figure 4:
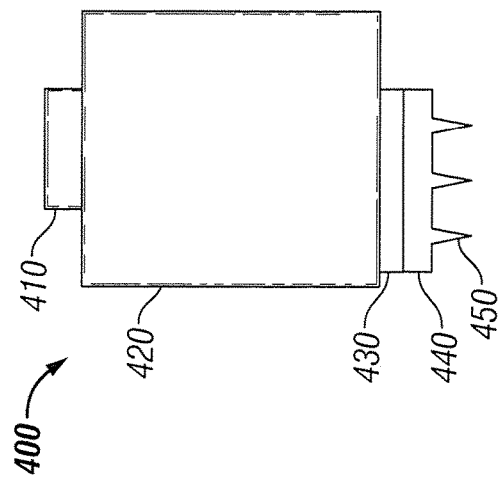

FIG. 4 depicts one embodiment of a drug delivery device 400 that includes a depressible portion 410 and a housing 420. Within the housing 420, the supporting layer 430 is movably mounted. The supporting layer 430 supports a substrate 440 from which an array of microneedles extends 450. The depressible portion includes a slanted surface 470 that corresponds to a slanted surface 460 of the supporting layer 430. Upon application of a force to the depressible portion 410, the array of microneedles 450 penetrates the tissue surface 480, and a shearing force is applied to the supporting layer 430 along with the substrate 440, which fractures the microneedles 490 of the array of microneedles 450. The device of FIG. 4 may be reconfigured to provide a rotational shearing force, for example, by incorporating two or more slanted surfaces on the depressible portion and/or supporting layer (or substrate).

In another embodiment, the supporting layer and the depressible portion have surfaces that engage one another at an interface, where the surfaces of that interface are configured to provide a high friction force between them (e.g., by surface irregularities, adhesive-type coatings, or the like) such that only upon application of a sufficient force is the frictional engagement at the interface overcome to permit displacement of the supporting layer and shearing of the microneedles.

The depressible portion, in embodiments, activates a shearing force by triggering at least one apparatus that applies the shearing force to the substrate and/or supporting layer.

In one embodiment, the apparatus that applies the shearing force includes one or more devices for storing elastic strain energy configured to apply the shearing force, such as a spring or other elastic material. The apparatus may be associated with a feature that releases the spring or other elastic material. The device for storing elastic strain energy may be stored in the device in an activated state (i.e., compressed or expanded state) or in a neutral state that is then either compressed or expanded during the application of the device to a biological tissue. The spring may be a resilient device, including, but not limited to, a helical metal coil or device having other geometries, that can be pressed or pulled but returns substantially to its former shape when released.

Figure 5:
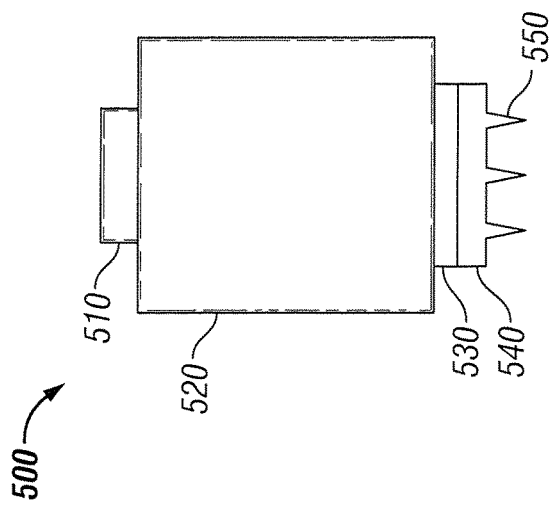
FIG. 5 depicts, in side and cross-sectional views, another embodiment of a drug delivery device having a depressible portion capable of imparting a lateral shearing force to separate microneedles that have been inserted into a biological tissue.

FIG. 5 depicts one embodiment of a drug delivery device 500 having a housing 520, a depressible portion 510, a supporting layer 530, and a substrate 540 from which an array of microneedles 550 extends. The device also has an apparatus that includes a spring 560 and a trigger 570. Upon depression of the depressible portion 510, the microneedles penetrate the tissue surface 580, and then the trigger 570 is activated, thereby releasing the spring 560, which applies a shearing force to the supporting layer 530. The application of the shearing force results in separated microneedles 590. The device of FIG. 5 may be reconfigured to provide a rotational shearing force, for example, by altering the point of contact between the spring and supporting layer, and/or using multiple springs. The trigger may be configured to swing out during activation to compress the spring further during insertion of the microneedles before releasing the shearing force. In this way, the trigger force may be controlled, and it permits the shearing force to occur only after the microneedles are inserted into the tissue by a predetermined amount.

In one embodiment, the apparatus that applies the shearing force includes an electronic element configured to apply the shearing force. The electronic element may generate the shearing force by at least one of a magnetic field and electric field. For example, the supporting layer and/or substrate may be associated with a magnet that responds to a magnetic field generated by the electronic element upon activation. The at least one apparatus may be configured to apply a rotational shearing force.

In another embodiment, the device includes magnets which in an initial device configuration are positioned far away from each other. In use, an input force pressing the device to insert the microneedles also causes the magnets to become closer to one another such that they interact (attract or repel) to trigger a shearing force. It is also envisioned that the device could be configured in a reverse scenario where the magnets interact before use and pressing on the device to insert the microneedles separates the magnets and thereby releases the shearing force.

In embodiments, at least one of the depressible portion, substrate, and supporting layer includes a threaded or spiraled portion that applies a shearing force to the supporting layer and/or substrate upon application of a force to the depressible portion. The shearing force may be rotational. In one embodiment, the depressible portion includes a threaded or spiraled rod that corresponds to a threaded orifice of the supporting layer and/or substrate. In another embodiment, the substrate and/or supporting layer includes a threaded rod that corresponds to a threaded orifice of the depressible portion. In a further embodiment, the depressible portion includes protrusions that correspond with spiraled tracking of the substrate and/or supporting layer. In another embodiment, the substrate and/or supporting layer includes protrusions that correspond with spiral tracking of the depressible portion. In yet another embodiment, the rotational motion is used to load a torsion spring, which then imparts rotational shear to the substrate or microneedles. To clarify, in various embodiments, a rotational output force may be applied throughout the application of the input force. Alternatively, the input force could provide an initial non-rotational output force, which later becomes a rotational output force.

Figure 6:
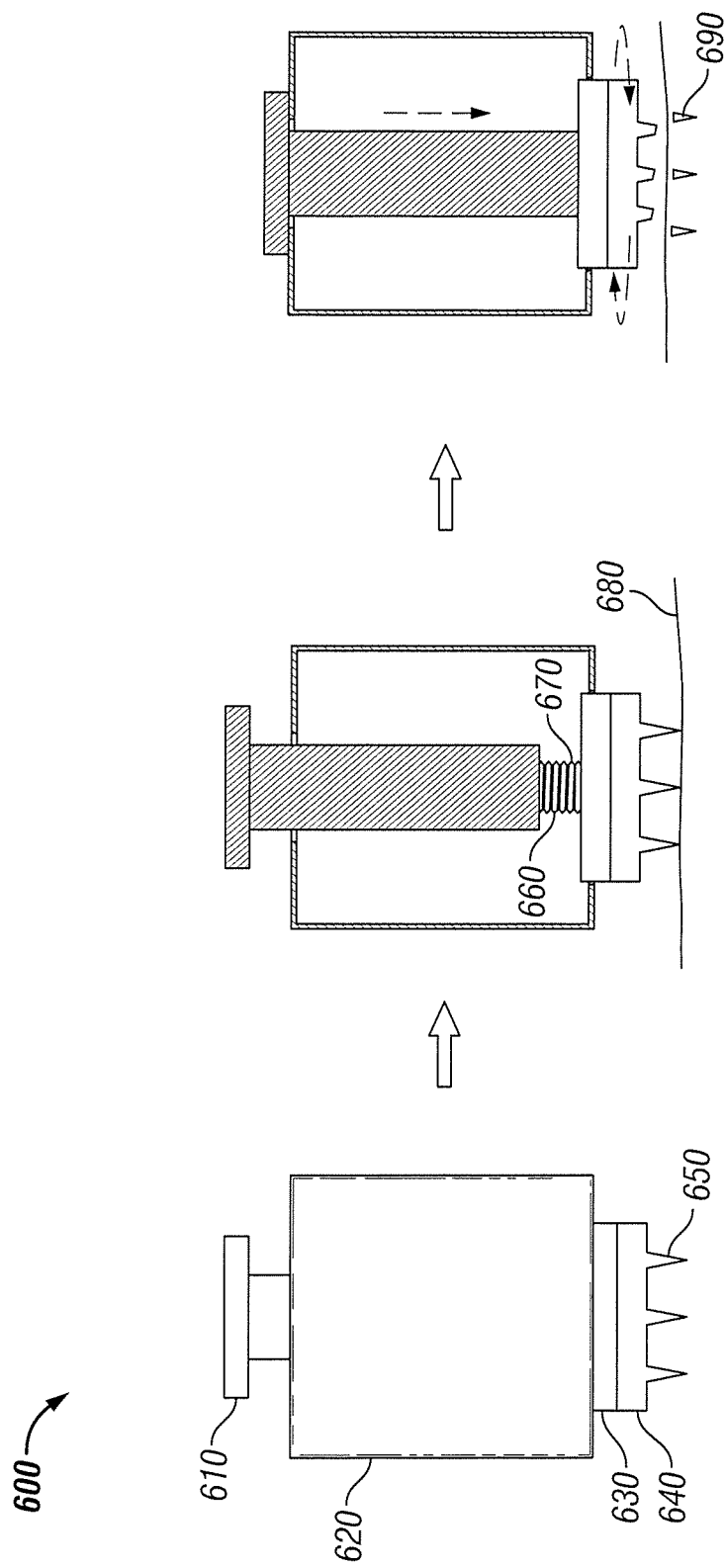
FIG. 6 depicts, in side and cross-sectional views, one embodiment of a drug delivery device having a depressible portion capable of imparting a rotational shearing force to separate microneedles that have been inserted into a biological tissue.

FIG. 6 depicts one embodiment of a drug delivery device 600 that includes a depressible portion 610 and a housing 620 in which a supporting layer 630 and substrate 640 are rotatably mounted. An array of microneedles 650 extends from the substrate 640. The depressible portion 610 includes a rod 660 with threading 670 that corresponds to a threaded orifice of the supporting layer 630, so that the application of force to the depressible portion 610 [1] penetrates the biological tissue surface 680 with the microneedles 650, and [2] applies a shearing force to the substrate 640 and supporting layer 630, resulting in the deposition of separated microneedles 690 beneath the surface of the biological tissue 680.

Systems for Triggering Change of Drug Release Rate

In embodiments, the drug delivery devices include a system for triggering, after the microneedles are inserted at least partially into a biological tissue, a change in rate of release of the drug from the microneedles and into the biological tissue. The release of drug from the drug delivery devices may be achieved by triggering events that take place gradually or at specific times upon or after deployment.

In embodiments, the system for triggering a change in rate of release of the drug allow for discrete periods of drug release to occur after the drug delivery devices are deployed. For example, for discrete periods after deployment the drug delivery devices may release little or no drug or one or more desired amounts of drug in any sequence. As a further example, the drug delivery devices, upon deployment, may allow little or no drug release for a first time period, a significant amount of drug release for a second time period, little or no release for a third time period, and a moderate amount of drug release for a fourth time period. Any sequence of these three drug releasing periods could be employed over at least two sequential periods. Also, a drug delivery device may include more than one drug, and each drug may have a different release profile.

In embodiments, the drug delivery devices include a drug with different release profiles at $t_1$, $t_2$, and $t_3$, as shown in the following table:

|  | T = 0 = microneedle insertion | $0 \leq t < t_1$ | $t_1 \leq t < t_2$ | $t_2 \leq t < t_3$ |
| --- | --- | --- | --- | --- |
| Embodiment 1 | No Release | Significant Release | Little or No Release | Significant Release |
| Embodiment 2 | No Release | Significant Release | Moderate Release | Little Release |
| Embodiment 3 | No Release | Little or No Release | Significant Release | Little or No Release |
| Embodiment 4 | No Release | Significant Release | No Release | No Release |

In one embodiment, the system for triggering release of a drug includes a first portion of the microneedles configured to bioerode at a greater rate than a second portion of the microneedles upon contact with a biological fluid. For example, the permeability change may allow tissue fluid (such as interstitial fluid) to penetrate the microneedles, and, as a result, allow the release of drug from the microneedles into the surrounding tissues via diffusion. Also, a change in osmotic pressure may cause or drive the release of drug. Changes in the surrounding environment or within the microneedles may lead to a change in osmotic pressure and result in the release of drug. For example, fluid from the surrounding environment, such as biological fluid, may enter the microneedles due to osmotic forces, which may help drive drugs out of the microneedles, and, if included in the drug delivery devices, a barrier as described herein. Convective flow driven by a pressure (including osmotic pressure) difference may also induce flow out of the microneedle, which can facilitate drug transport out of the microneedle.

In one embodiment, the system for triggering drug release includes a change in binding between the drug and another molecule in the microneedles. The other molecule may be an excipient. The binding may be covalent or non-covalent. The binding may retain the drug within the microneedles until a change in drug binding allows the release of the drug from the microneedles. The strength of the binding/affinity between drug and microneedles may be tailored to release drug slowly from microneedles into surrounding tissues. This may be achieved, for example, by relying on specific intermolecular forces, such as ionic bonds, hydrogen bonds, or van der Waals forces, to achieve a given release profile.

In one embodiment, the system for triggering drug release includes a change in the diffusivity of drug. The change in diffusivity may be caused by a change of the [1] charge (pH) of a drug and/or another molecule in the microneedles, [2] hydrophilicity or hydrophobicity of a drug and/or another molecule in the microneedles, [3] molecular size/shape of a drug and/or another molecule in the microneedles, [4] shape/conformation of a drug and/or another molecule in the microneedles, or [5] a combination thereof. A decrease in the size (mass) of molecules can lead to increased diffusion of drug. The change in molecular size can be the result of breaking covalent bonds (e.g., degradation) or the result of breaking weaker bonds (e.g., unbinding/binding, deaggregation/aggregation). Drugs may be covalently linked to a component of the microneedles, and such covalent bonds may be cleaved enzymatically, chemically, or via a change in pH. The change in shape/conformation of drug can influence its rate of release, sometimes in a non-linear manner because a small change in shape/conformation can have a large effect on release from the microneedles because there may be a pore or other transport pathway that is of similar size as the drug molecule, such that a conformational change could determine whether the drug molecules can pass through the pathway easily, if at all. A change in conformation also may affect which regions of the drug molecule are sequestered in the interior of the molecule and which are exposed on the molecule's outer surface. The resulting difference in surface properties of the molecule may affect its interaction with the surrounding medium and thereby have a different release rate due to changes in attractive and repulsive forces (e.g., hydrophobicity, charge). A change in shape/conformation may be induced by changes in temperature, pH, ionic strength, other techniques known in the art, or a combination thereof. The strength of the binding/affinity may be varied during deployment of the drug delivery devices to alter, i.e., increase or decrease, the release of drug. This may be the result of an external stimulus (e.g., the user triggers the change in binding strength) or as a result of an internal stimulus (e.g., a chemical or biological change within the user triggers the change in binding/affinity strength).

In one embodiment, the system for triggering drug release includes a structural change of the microneedles. The structural change may include separable microneedles, such as those described herein. The structural change, including separation of the microneedles, may result in a drug being released from the microneedles upon or after exposure to surrounding tissues or fluids following the structural change.

In one embodiment, the system for triggering drug release includes a change in shape of the microneedles. For example, a tip or outer layer of the microneedles may dissolve first, thereby exposing drugs within the microneedles to biological tissues and fluids.

In embodiments, the system for triggering drug release includes a change of one or more properties of tissues targeted and/or surrounded by the drug delivery devices upon deployment. In one embodiment, blood flow/perfusion may be increased or decreased in tissues in the proximity of the microneedles' insertion site and, as a result, affect the release and uptake of drug. Blood flow/perfusion may be modulated by relying on [1] temperature (e.g., applying heat or cooling drug delivery device and/or insertion site/area), [2] mechanical forces (e.g., applying pressure, rubbing, vibration, use of a ring/tourniquet), [3] chemical methods (e.g., bioactives, irritants, vasodilators, vasoconstrictors), and [4] a combination thereof. In another embodiment, tissue permeability and/or convective flow may be varied to achieve an increase or decrease in drug release. Changes in tissue permeability/convective flow may be achieved [1] chemically/biochemically (e.g., hyaluronidase may be used to degrade the extracellular matrix, or changes in interstitial fluid pressure also may be achieved to alter active uptake by surrounding tissues), [2] physically (e.g., temperature, pressure, water content, mechanical (including mechanical damage to tissue, such as by microneedles), electroporation, thermal perturbation/damage, ultrasound, cavitation, laser, radiofrequency energy are all means to alter tissue permeability), or [3] a combination thereof. In a further embodiment, material from biological tissue or extracellular matrix interacts with or covers, enters, and/or obstructs microneedles to change the drug release rate. For example, water may enter microneedles to dissolve material and/or an analyte from tissue may displace a bound drug. In still another embodiment, driving forces that transport drug from microneedles and through tissue are modulated. Driving forces that can affect the rate of release of actives can be modulated to control the drug release profile. Driving forces that can be modulated include [1] electrophoresis, [2] electro-osmosis, [3] concentration gradient (which, when increase, may enhance clearance of drug from tissue by blood flow, lymphatic flow, metabolism, other active and passive transport processes (or the reverse), [4] pressure gradient (e.g., ultrasound, mechanical perturbation, rubbing/vibration, e.g., to cause convection), or [5] a combination thereof.

In one embodiment, the system for triggering includes a barrier material positioned in or on at least part of the microneedle. The barrier provided by the barrier material, in embodiments, impedes release of the drug from the microneedle in at least one direction and/or for a predetermined period of time.

In embodiments, the system for triggering changes the rate of release in response to one or more of the following: analyte concentration, temperature, pH, pressure, electric field, magnetic field, electrical charge, electrical current, vibration, ultrasound, shearing force, mechanical movement/perturbation, molecule/cell binding, moisture/water content of the microneedles, time, diffusion of species from the microneedles, dissolution, degradation, chemical reaction, other mechanisms known in the art, or a combination thereof. Other mechanisms known in the art include those disclosed at Siepmann, J. et al., "Fundamentals and Applications of Controlled Release Drug Delivery," $1^{st}$ Edition, 2012, XIII, p. 592; Li, X., "Design of Controlled Release Drug Delivery Systems, McGraw-Hill Chemical Engineering, Nov. 3, 2005; and Wise, Donald L., Handbook of Pharmaceutical Controlled Release Technology, CRC Press, Aug. 24, 2000.

In embodiments, the system for triggering changes the rate of drug release in response to a change of pH. For example, the change of pH may be a lowering of pH in response to increased glucose concentration, and the resulting lower of pH may cause the system for triggering to release or increase the release of insulin from a drug delivery device provided herein.

In embodiments, the system for triggering changes the rate of drug release in response to a change of temperature. External or internal (to the body) modulation of temperature, therefore, may modulate drug release from the drug delivery devices.

In embodiments, the system for triggering changes the rate of drug release in response to mechanical movement/perturbation, vibration, or a combination thereof. The mechanical movement/perturbation and/or vibration may be applied to the drug delivery devices and/or the surrounding tissues by the drug delivery devices or an external user to modulate drug release.

In embodiments, the system for triggering a change of drug release rate includes partially inserting one or more microneedles of an array of microneedles, allowing drug release from a first part of the microneedles, and then completely or further inserting the one or more microneedles, allowing drug release from a second part of the microneedles. Partial insertion of microneedles into biological tissue may allow for partial dissolution of microneedles, e.g., dissolution of only the part of the microneedles that is inserted, although more of the microneedles may dissolve if tissue fluids reach by diffusion or capillary forces parts of the microneedles on or above the skin surface that are not yet inserted. When partial insertion occurs, the drug associated with the portion of the microneedles may be released. These techniques may be used to modulate the quantities and release kinetics of one or more drugs within a drug delivery device. For example, initial partial insertion and dissolution of microneedles might allow an initial release/burst of drug followed by additional releases at specific time points or in a continuous or semi-continuous fashion over a period of time. These techniques also may be used to deliver different drugs in sequence when different parts of the microneedles contain different drugs. For example, the tip of the microneedles could contain drug "A" and the rest of the microneedles' bodies could contain drug "A" or a different drug, drug "B." Following insertion of the tips only, drug "A" would be released, and further insertion may permit release of an additional amount of drug "A" or the release of drug "B." In each of the foregoing scenarios, the amount/degree of microneedles insertion and the period over which partial or full microneedle insertion occurs can be varied.

Each of the foregoing mechanisms may be used alone or in any combination in the system for triggering a change of drug release. Each of the foregoing mechanisms also may include increasing or decreasing the concentration of the drug and/or excipients in the microneedles. Doing so may alter the concentration gradient, which drives transport by diffusion, and can also alter the amount of drug moved by other mechanisms, such as convection and electrically driven transport. Increasing or decreasing the concentration of excipients can alter the rate at which drug moves through the environment containing the excipients, such as altering the drug diffusivity/mobility, the medium viscosity, the medium porosity and other factors.

Barrier

In embodiments, the system for triggering change of drug release rate is a barrier that may be positioned in or on at least part of the microneedle to impede release of the drug from the microneedle in at least one direction and/or for a predetermined period of time. In one embodiment, the barrier is configured to permit (i) discrete periods of drug release upon or after implantation, (ii) control of the region of the microneedles from which the drug is released, or (iii) a combination thereof. The term "barrier" and the phrase "barrier material" are used interchangeably herein.

In embodiments, the barrier impedes release of a drug from the microneedle until the barrier no longer obstructs release of the drug. The obstruction provided by the barrier may be permanent, or lessened gradually or substantially instantaneously.

A barrier generally may be positioned in a microneedle, on a microneedle, or a combination thereof. For example, a barrier may at least partially encapsulate a drug in a microneedle, be dispersed within the matrix of one or more microneedles, be positioned on and/or at the surface of one or more microneedles, or a combination thereof. When dispersed within the matrix of one or more microneedles, the barrier may include discrete regions within the matrix. When a barrier encapsulates a drug, a drug delivery device may include one drug encapsulated with different amounts/concentrations of one or more barrier materials, two or more drugs encapsulated with different amounts/concentrations of the same or different barrier materials, or a combination thereof.

Figure 7:
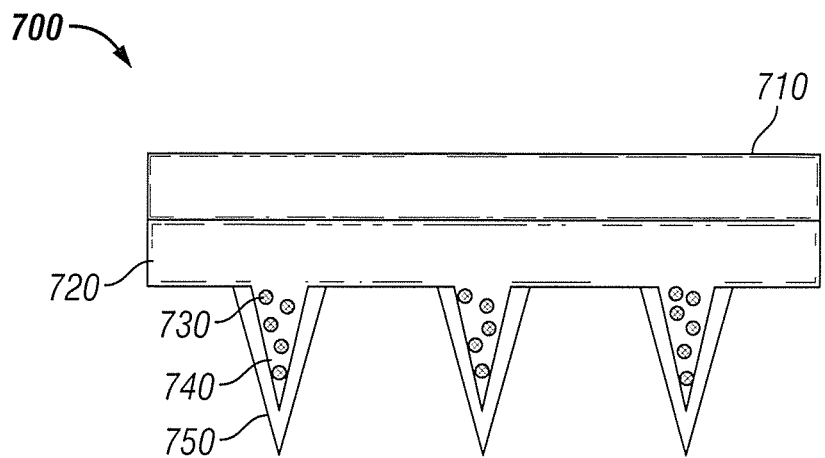
FIG. 7 depicts, in a cross-sectional view, one embodiment of a drug delivery device having microneedles coated with a barrier.

FIG. 7 depicts one embodiment of a drug delivery device 700 that includes a barrier positioned on the surface of microneedles. The drug delivery device includes a supporting layer 710, a substrate 720, and an array of microneedles 740 including a drug 730, which extend from the substrate 720. Each microneedle 740 has a barrier material 750 positioned on its surface.

In embodiments, the microneedles themselves act as barriers when drug is disposed in the substrate.

In embodiments, at least a portion of the barrier is configured to be permanent. In other words, the barrier is configured to remain in place upon and after deployment, and is substantially impervious to all mechanism that may remove or lessen the obstruction provided by the barrier.

The barrier or barrier material may include one or more different materials. The barrier may include two or more different materials, each associated with the same or different portions of the drug delivery devices. When associated with the same portion of a drug delivery device, the two or more materials may form a multi-layered barrier material. Alternatively, the barrier may include two materials, each coating a separate portion of a microneedle; or the barrier may include two materials, the first material being a liquid disposed in a second material that is a solid.

A single microneedle array may include two or more types of barriers. For example, an array could include one row of microneedles having a barrier of a first type and a second row of microneedles having a barrier of a second type. For example, the differences could be beneficially designed for delivering two different substances of interest.

In one embodiment, the barrier material includes a first coating positioned in or on at least a first portion of one or more microneedles of the array of microneedles. The first coating may be at least substantially inert in biological fluid (e.g., insoluble) and unchanged upon and after deployment, and prevent drug release from the first portion of one or more microneedles of the array of microneedles. Alternatively, barrier material includes a first coating having one or more properties, such as permeability or porosity, that change upon or after contacting a biological fluid, and therefore permits drug release from the first portion of one or more microneedles of the array of microneedles. The first coating, for example, may be at least partially soluble in biological fluid. In another embodiment, the barrier material also includes a second coating positioned in or on a second portion of one or more microneedles of the array of microneedles. The first coating may be inert (e.g., insoluble) and unchanged upon and after deployment in biological tissue and fluid, and the second coating may have one or more properties, such as porosity and/or permeability, that change upon deployment, thereby permitting drug release to occur only from the second portion of one or more microneedles of the array of microneedles.

In one embodiment, the barrier material includes a first coating positioned in or on at least a first portion of one or more microneedles of the array of microneedles, and a second coating positioned in or on a second portion of one or more microneedles of the array of microneedles. The first and second coatings may permit drug release at different times upon deployment, therefore allowing two drugs to be released simultaneously, sequentially, or a combination thereof.

In embodiments, the obstruction provided by at least a portion of the barrier is removed, gradually or completely, upon or after the onset of dissolution of a barrier material, swelling/expansion of a barrier material, chemical reaction/degradation of a barrier material, vaporization of a barrier material, solidification of a barrier material, melting of a barrier material, gelling of a barrier material, deformation/breaking/collapsing/contracting of a barrier material, change of charge state of a barrier material, or a combination thereof. The composition of the barrier material may be selected or formulated so that its dissolution rate allows it to achieve a desired drug release profile.

In embodiments, the obstruction provided by at least a portion of the barrier is removed, gradually or completely, upon or after a change in binding/affinity between the barrier and drug. Binding/affinity between drug and a barrier may be used, therefore, to achieve a specific drug release profile, or modulate a drug release profile. Binding/affinity between the barrier and drug may be achieved by any techniques known in the art. For example, binding/affinity may be charge-mediated, i.e., based on the respective charge state of each component. The charge state, as explained herein, may be changed by modulating pH. A change in pH can be used to increase or decrease the charge state of drug and/or barrier materials. As pH decreases, basic drugs may become more charged, and acidic drugs become less charged. Also, a voltage or electric field may be applied to at least a portion of the drug delivery devices, resulting in a change in the charge distribution on the drugs, which results in a change in binding strength/affinity. As a further example, the binding of drug to a barrier material may vary based on the presence or introduction of other molecules or species having higher affinity for the barrier material than the drug. Binding/affinity also may be modulated by pH, temperature, pressure, ionic strength, competitive binding, chemical reactions, or a combination thereof.

In one embodiment, the obstruction provided by at least a portion of the barrier is removed, gradually or completely, upon or after the onset of dissolution of a barrier material. Therefore, the barrier may be formed with a barrier material, such as a salt, that dissolves upon exposure to a biological fluid at the tissue site of insertion, or a polymer that degrades via hydrolysis. For example, a salt having low aqueous solubility may delay release of the active. In embodiments, upon dissolution of a barrier material, at least a portion of a microneedle is exposed to biological tissue and/or fluid, thereby permitting release of drug from the portion of the microneedle associated with the barrier material. In further embodiments, upon dissolution of a barrier material, the porosity within the microneedle may be increased, thereby permitting release of drug.

Figure 8A:
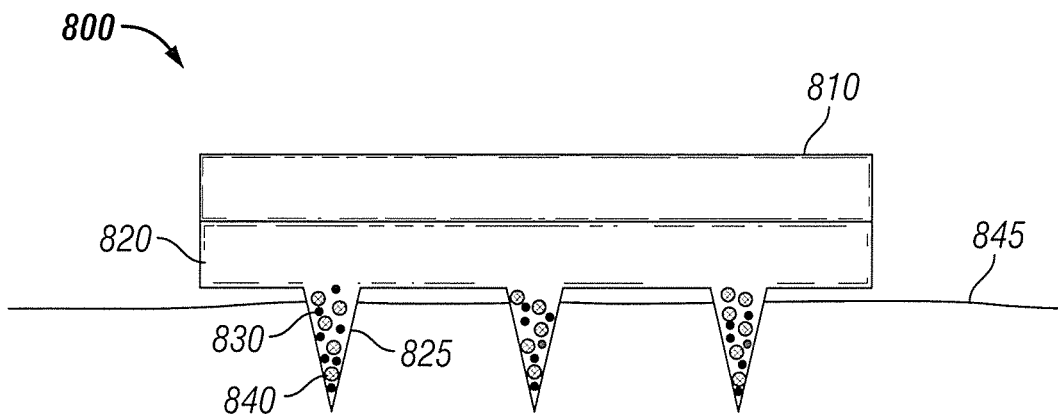
FIG. 8A depicts, in a cross-sectional view, one embodiment of a drug delivery device including barrier particles in the microneedles.
Figure 8B:
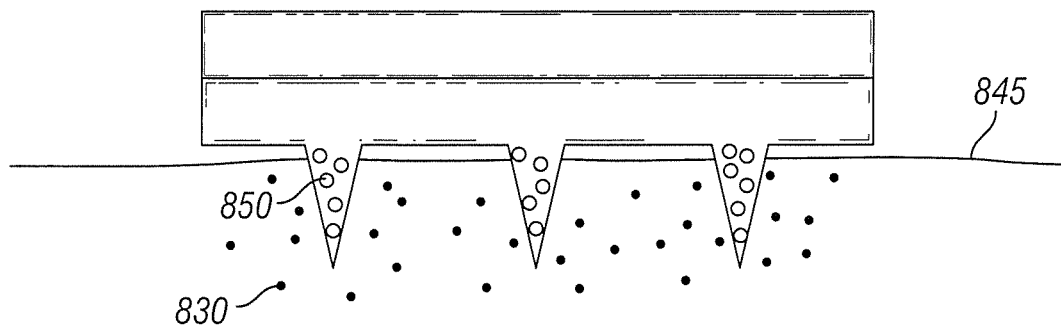
FIG. 8B depicts, in a cross-sectional view, release of drug from the embodiment of a drug delivery device shown in FIG. 8A.

One embodiment of a drug delivery device including a bioerodible barrier material is depicted at FIG. 8A and FIG. 8B. The drug delivery device 800 includes a supporting layer 810 and a substrate 820 from which microneedles 825 extend. The microneedles 825 include drug 830 and discrete portions of a bioerodible barrier material 840. Upon dissolution or other degradation of the barrier material 840 after the microneedles penetrate the tissue surface 845, pores 850 are created in the microneedles, which permits release of the drug 830.

Figure 9A:
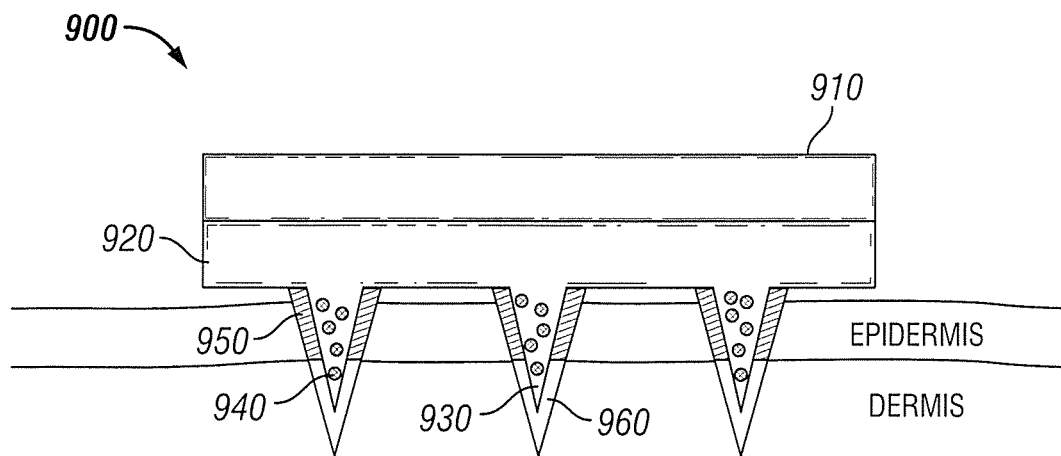
FIG. 9A depicts, in a cross-sectional view, one embodiment of a drug delivery device having microneedles coated with a barrier including two different materials.
Figure 9B:
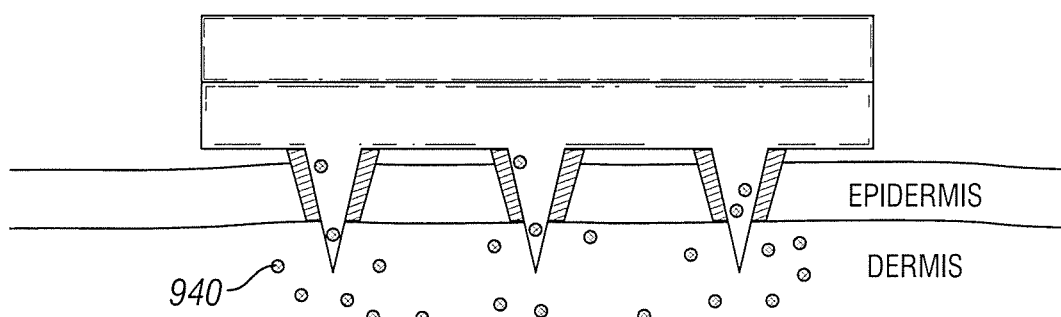
FIG. 9B depicts, in a cross-sectional view, release of drug from the embodiment of a drug delivery device shown in FIG. 9A.

One embodiment of a drug delivery device included a barrier having a bioerodible portion and a (relatively) non-bioerodible portion is depicted at FIG. 9A and FIG. 9B. FIG. 9A depicts a drug delivery device 900 having a supporting layer 910 and a substrate 920 from which microneedles 930 extend. The microneedles include a drug 940, and are associated with a barrier material that includes a first coating 950 that is permanent and insoluble in biological fluids, and a second coating 960 that is soluble in biological fluid. Upon penetration of skin, the second coating 960 dissolves, as shown at FIG. 9B, thereby permitting the drug 940 to be released at the dermis, while the first coating 950 remains intact, thereby prohibit drug release at the epidermis. In an alternative embodiment, the portion of the barrier 950 associated with the epidermis is soluble in biological fluid, and the portion of the barrier 960 associated with the dermis is insoluble and permanent, therefore resulting in release of the drug only into the epidermis.

In one embodiment, the obstruction provided by at least a portion of the barrier may be removed, gradually or completely, upon or after the onset of swelling/expansion of the barrier material. Therefore, the barrier may be formed with a barrier material, such as a gel, that expands upon exposure to a biological fluid, temperature, other stimuli, or a combination thereof, thereby increasing the permeability of the biological material, which permits the release of drug. For example, the drug delivery devices, including the microneedles, may include a channel that is at least partially filled with a gel, so that the ability of drug to traverse the channel is increased or decreased as the gel contracts or expands, respectively.

In one embodiment, the obstruction provided by at least a portion of the barrier is removed, gradually or completely, upon or after the onset of a chemical reaction and/or degradation of a barrier material. The barrier material, upon or after exposure to biological fluids, may undergo changes in its physicochemical properties as a result of chemical, physical, mechanical, and/or biological interactions with a biological tissue. Therefore, degradation of the barrier material may occur. In embodiments, in which the barrier material is a polymeric material, degradation may be initiated, upon or after contact with biological fluid, by hydrolytic scission of polymer chains, which may result in bulk degradation and/or surface erosion of the polymer. Degradation also may occur by enzymatic degradation.

In one embodiment, the obstruction provided by at least a portion of the barrier is removed, gradually or completely, upon or after vaporization of a liquid included in a barrier material. The vaporization of the liquid may change the permeability and/or porosity of the barrier material, or create or expose pores within microneedles. The vaporization may be triggered by evaporation, boiling, acoustic droplet vaporization, or by other means known in the art. The liquid that vaporizes may be formed within the barrier prior to deployment of the drug delivery devices, or biological fluid that penetrates the barrier material upon or after deployment.

In one embodiment, the obstruction provided by at least a portion of the barrier is removed, gradually or completely, upon or after solidification of a barrier material, such as an aquamelt, which typically is a naturally hydrated polymeric material capable of solidifying at certain temperatures through a controlled stress input, including mechanical or chemical input. Aquamelts made from chitin, fibroin, or a combination thereof may be used. The solidification may be initiated upon or after exposure to biological fluid, or upon or after exposure to the environment prior to deployment. Upon or after solidification, the permeability of the barrier material is increased.

In one embodiment, the obstruction provided by at least a portion of the barrier may be removed, gradually or completely, upon or after melting of a barrier material. Melting may be initiated following insertion of microneedles into biological tissue, upon exposing the microneedles to the environment upon or after removal from their packaging, by application of heat by an external source, or a combination thereof. For example, a drug delivery device stored in freezing conditions may include water as a barrier material, and the water melts upon exposure to ambient conditions, biological fluid, or a combination thereof.

In one embodiment, the obstruction provided by the barrier is removed, gradually or completely, upon or after a change of charge state of a barrier material. For example, a barrier material may be or become charged prior to or after deployment, respectively, and then the charge of the barrier material changes or is lost. The change of charge state of a barrier material may be used to control drug release. In embodiments, a barrier material and drug have opposite charge states, and the repulsion force is used to retain the drug in the microneedles until the charge of the barrier material is changed or lost. In further embodiments, a barrier material and drug have the same charge state, and the attraction between the barrier material and drug is used to retain the drug in the microneedles until the charge state of the barrier material changes or is lost.

Also, a change in charge state of the barrier and/or drug may alter the release of drug under the effect of an electric field. The release may also be caused by the application of a change in electric field. For example, an electric field may be applied across the microneedles and the targeted tissue, and optionally at discrete time points to affect the kinetics of the release. The application of the electric field or change in field strength and/or direction may trigger the release from the matrix of charged drug. A change of charge may be effected by a change of pH or ionic strength (which shields the charge) or other factors. Also, electrophoresis also may be used to drive charged particles or drugs from the microneedles and/or through a barrier. Electroosmosis may also be used to drive liquid containing an active across a charged barrier.

In one embodiment, the obstruction provided by at least a portion of the barrier is removed, gradually or completely, upon or after deformation, breaking, collapsing, and/or contraction of a barrier material. A barrier material may deform, break, collapse, and/or contract upon exposure to compression, tension, shear, torque, vibrations, ultra-sound, or a combination thereof. One or more of these forces may be applied to any portion of the drug delivery devices. For example, in the device depicted at FIG. 9A, the portion of the barrier 960 associated with the dermis could have been configured to fail by breaking, deforming, collapsing, or contracting, as opposed to dissolving.

In one embodiment, the obstruction provided by at least a portion of the barrier is permanent. A permanent barrier, for example, may prevent one or more microneedles from releasing drug from the region associated with the permanent barrier. Therefore, the permanent barrier may ensure that the microneedle is capable of releasing drug only from areas not obstructed by the permanent barrier, including areas exposed by the separation of microneedles.

Figure 10A:
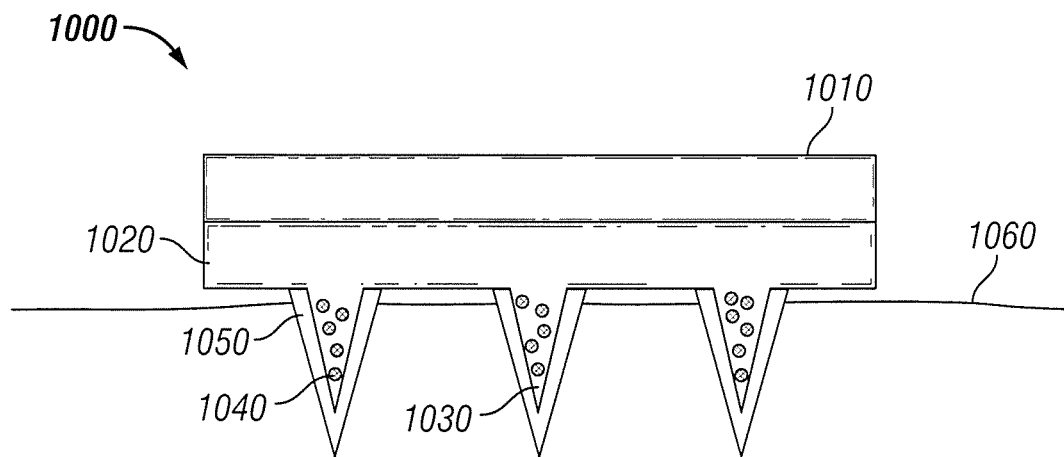
FIG. 10A depicts, in a cross-sectional view, another embodiment of a drug delivery device having microneedles coated with a barrier.
Figure 10B:
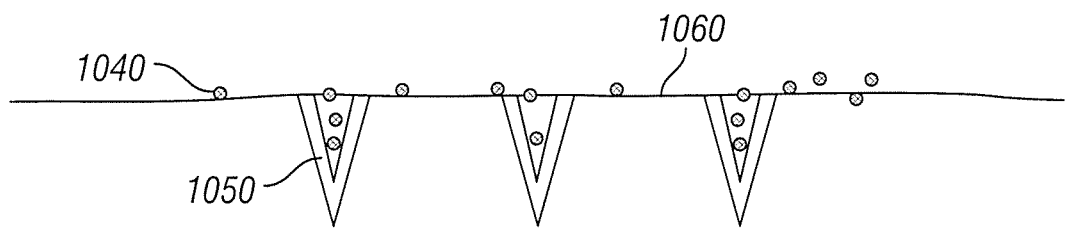
FIG. 10B depicts, in a cross-sectional view, release of drug from the microneedles separated from the drug delivery device shown in FIG. 10A.

One embodiment of a drug delivery device having separable microneedles and a permanent barrier is depicted at FIG. 10A and FIG. 10B. The drug delivery device 1000 of FIG. 10A includes a supporting layer 1010 and microneedles 1030 extending from a substrate 1020. The microneedles include a drug 1040 and each of the microneedles 1030 are coated with a permanent barrier 1050, so that upon separation of the microneedles, as depicted at FIG. 10B, the drug 1040 is released primarily to the tissue surface 1060 because the barrier 1050 remains in place, thereby preventing drug release beneath the tissue surface 1060.

Supporting Layer

The supporting layer may be adhered to the substrate by any means known in the art, including an adhesive. In one embodiment, an adhesive layer is use to adhere the supporting layer to the substrate.

The supporting layer may be made out of a variety of materials. In some embodiments, the supporting layer may be a composite material or multilayer material including materials with various properties to provide the desired properties and functions. For example, the supporting layer may be flexible, semi-rigid, or rigid, depending on the particular application. As another example, the supporting layer may be substantially impermeable, protecting the one or more microneedles (or other components) from moisture, gases, and contaminants.

Alternatively, the supporting layer may have other degrees of permeability and/or porosity based on the desired level of protection that is desired. Non-limiting examples of materials that may be used for the supporting layer include various polymers, elastomers, foams, paper-based materials, foil-based materials, metallized films, and non-woven and woven materials.

An optional mechanical force indicator may be disposed between the supporting layer and the substrate, or it may be located within or be an integral part of the supporting layer. The mechanical force indicator may be used to indicate to a person the amount of force and/or pressure applied to the drug delivery device during its use. For example, in one embodiment, the indicator is configured to provide a signal when a force applied to the drug delivery device by a person (in the course of applying the drug delivery device to a patient's skin to insert the one or more microneedles into the patient's skin) meets or exceeds a predetermined threshold. The predetermined threshold may be the minimum force or some amount greater than the minimum force that is required for a particular drug delivery device to be effectively applied to a patient's skin. In other words, it may be the force needed to cause the microneedles to be properly, e.g., partially or fully, inserted into a patient's skin; or it may be the force needed to cause the microneedles to be properly, e.g., partially or fully, inserted into a patient's skin, and separate the microneedles from the substrate.

Methods of Using the Drug Delivery Devices

As used herein, the phrase "penetrate a tissue surface" or the terms "penetrate" or "penetration" refers to the insertion of at least 50%, and typically substantially all, of the microneedles of an array of microneedles, including at least the tip or distal end portion of the microneedles, into a biological tissue. In a preferred embodiment, the "penetration" includes piercing the stratum corneum of the skin of a human patient such that at least the tip end portion of the microneedle is within or has passed across the viable epidermis.

The drug delivery devices provided herein may be self-administered or administered by another individual (e.g., a parent, guardian, minimally trained healthcare worker, expertly trained healthcare worker, and/or others).

Thus, embodiments provided herein further include a simple and effective method of administering a substance of interest with a drug delivery device. The methods provided herein may include identifying an application site and, preferably, sanitizing the area prior to application of the drug delivery device (e.g., using an alcohol wipe). The drug delivery device then is applied to the patient's skin/tissue and manually pressed into the patient's skin/tissue (e.g., using the thumb or finger) by applying a force as described herein.

After administration is complete, the substrate, supporting layer, housing, and/or depressible portion may be removed from the patient's skin/tissue in embodiments having separable microneedles. In embodiments, the drug delivery devices described herein are used to deliver one or more substances of interest (e.g., vaccines, therapeutics, vitamins) into the body, tissue, cells, and/or organ. In one embodiment, the drug delivery devices are used to deliver the active into skin by inserting the microneedles across the stratum corneum (outer 10 to 20 microns of skin that is the barrier to transdermal transport) and into the viable epidermis and dermis. The small size of the microneedles enables them to cause little to no pain and target the intradermal space. The intradermal space is highly vascularized and rich in immune cells and provides an attractive path to administer both vaccines and therapeutics. The microneedles are preferably dissolvable and once in the intradermal space they dissolve within the interstitial fluid and release the active into the skin. In embodiments that include separable microneedles, the substrate can be removed and discarded upon or after separation of the microneedles, which preferably is nearly immediately upon insertion.

In one embodiment, a method is provided for administering a substance of interest to a patient, which includes providing one of the microneedle arrays described herein; and applying the microneedles of the array to a tissue surface of the patient, wherein the insertion of the microneedles of the array into the skin is done manually without the use of a separate or intrinsic applicator device. In this particular context, the term "applicator device" is a mechanical device that provides its own force, e.g., via a spring action or the like, which serves as the primary force to drive the microneedle array against the tissue surface, separate from any force the user may impart in holding the device and/or microneedles against the tissue surface.

Substance of Interest/Active Pharmaceutical Ingredient

A wide range of substances may be formulated for delivery to biological tissues with the present microneedles and methods. As used herein, the term "substance of interest" includes active pharmaceutical ingredients, allergens, vitamins, cosmetic agents, cosmeceuticals, diagnostic agents, markers (e.g., colored dyes or radiological dyes or markers), and other materials that are desirable to introduce into a biological tissue. The "substance of interest" is sometimes referred to herein as "the active" or an "API" or a "drug".

In one embodiment, the substance of interest is a prophylactic, therapeutic, or diagnostic agent useful in medical or veterinary application. In one embodiment, the substance of interest is a prophylactic or therapeutic substance, which may be referred to herein as an API. In certain embodiments, the API is selected from suitable proteins, peptides and fragments thereof, which can be naturally occurring, synthesized or recombinantly produced. Representative examples of types of API for delivery include antibiotics, antiviral agents, analgesics, anesthetics, antihistamines, anti-inflammatory agents, anti-coagulants, allergens, vitamins, antineoplastic agents.

In one embodiment, the substance of interest comprises a vaccine. Examples of vaccines include vaccines for infectious diseases, therapeutic vaccines for cancers, neurological disorders, allergies, and smoking cessation or other addictions. Some examples of current and future vaccines for the prevention of, anthrax, cervical cancer (human papillomavirus), dengue fever, diphtheria, Ebola, hepatitis A, hepatitis B, hepatitis C, *Haemophilus influenzae* type b (Hib), HIV/AIDS, human papillomavirus (HPV), influenza (seasonal and pandemic), Japanese encephalitis (JE), lyme disease, malaria, measles, meningococcal, monkeypox, mumps, pertussis, pneumococcal, polio, rabies, rotavirus, rubella, shingles (herpes zoster), smallpox, tetanus, typhoid, tuberculosis (TB), varicella (chickenpox), West Nile, and yellow fever.

In another embodiment, the substance of interest comprises a therapeutic agent. The therapeutic agent may be selected from small molecules and larger biotechnology produced or purified molecules (e.g., peptides, proteins, DNA, RNA). Examples of therapeutics, which may include their analogues and antagonists, include but are not limited to insulin, insulin-like growth factor, insultropin, parathyroid hormone, pramlintide acetate, growth hormone release hormone, growth hormone release factor, mecasermin, Factor VIII, Factor IX, antithrombin III, protein C, protein S, β-gluco-cerebrosidase, alglucosidase-a, laronidase, idursulphase, galsulphase, agalsidase-β, a-1 proteinase inhibitor, lactase, pancreatic enzymes, adenosine deaminase, pooled immunoglobulins, human albumin, erythropoietin, darbepoetin-a, filgrastim, pegfilgrastim, sargramostim, oprelvekin, human follicle-stimulating hormone, human chorionic gonadotropin, lutropin-a, interferon (alpha, beta, gamma), aldesleukin, alteplase, reteplase, tenecteplase, urokinase, factor Vila, drotrecogin-a, salmon calcitonin, exenatide, octreotide, dibotermin-a, recombinant human bone morphogenic protein 7, histrelin acetate, palifermin, becaplermin, trypsin, nesiritide, botulinum toxin (types A and B), collagenase, human deoxyribonuclease I, hyaluronidase, papain, 1-asparaginase, peg-asparaginase, rasburicase, lepirudin, bivalirudin, streptokinase, anistreplase, bevacizumab, cetuximab, panitumumab, alemtuzumab, rituximab, trastuzumab, abatacept, anakinra, adalimumab, etanercept, infliximab, alefacept, efalizuman, natalizumab, eculizumab, antithymocyte globulin, basiliximab, daclizumab, muromonab-CD3, omalizumab, palivizumab, enfuvirtide, abciximab, pegvisomant, crotalidene polyvalent fab (ovine), digoxin immune serum fab (ovine), ranibizumab, denileukin diftitox, ibritumomab tiuxetan, gemtuzumab ozogamicin, tositumomab, I-tositumomab, anti-rhesus (rh) immunoglobulin G, desmopressin, vasopressin, deamino [Val4, D-Arg8] arginine vasopressin, somatostatin, somatotropin, bradykinin, bleomycin sulfate, chymopapain, glucagon, epoprostenol, cholecystokinin, oxytocin, corticotropin, prostaglandin, pentigetide, thymosin alpha-1, alpha-1 antitrypsin, fentanyl, lidocaine, epinephrine, sumatriptan, benztropine mesylate, liraglutide, fondaparinux, heparin, hydromorphone, omacetaxine mepesuccinate, pramlintide acetate, thyrotropin-alpha, glycopyrrolate, dihydroergotamine mesylate, Bortezomib, triptoreline pamaote, teduglutide, methylnaltrexone bromide, pasireotide, ondansetron hydrochloride, droperidol, triamcinolone (hex)acetonide, aripiprazole, estradiol valerate, morphine sulfate, olanzapine, methadone hydrochloride, and methotrexate.

In yet another embodiment, the substance of interest is a vitamin, herb, or dietary supplement known in the art. Non-limiting examples include 5-HTP (5-hydroxytryptophan), acai berry, acetyl-L-carnitine, activated charcoal, aloe vera, alpha-lipoic acid, apple cider vinegar, arginine, ashitaba, ashwagandha, astaxanthin, barley, bee pollen, beta-alanine, beta-carotene, beta-glucans, biotin, bitter melon, black cherry, black cohosh, black currant, black tea, branched-ahain amino acids, bromelain (bromelin), calcium, camphor, chamomile, chasteberry, chitosan, chlorella, chlorophyll, choline, chondroitin, chromium, cinnamon, citicoline, coconut water, coenzyme Q10, conjugated linoleic acid, cordyceps, cranberry, creatine, D-mannose, damiana, deer velvet, DHEA, DMSO, echinacea, EDTA, elderberry, emu Oil, evening primrose oil, fenugreek, feverfew, folic acid, forskolin, GABA (gamma-aminobutyric acid), gelatin, ginger, *Ginkgo biloba*, ginseng, glycine, glucosamine, glucosamine sulfate, glutathione, gotu kola, grape seed extract, green coffee, guarana, guggul, gymnema, hawthorn, hibiscus, holy basil, horny goat weed, inulin, iron, hill oil, L-carnitine, L-citrulline, L-trypotophan, lactobacillus, magnesium, magnolia, milk thistle, MSM (methylsulfonylmethane), niacin, olive, omega-3 fatty acids, oolong tea, oregano, passionflower, pectin, phenylalanine, phosphatidylserine, potassium, probiotics, progesterone, quercetin, ribose, red yeast rice, reishi mushroom, resveratrol, rosehip, saffron, SAM-e, saw palmetto, schisandra, sea buckthorn, selenium, senna, slippery elm, St. John's wort, stinging nettle, tea tree oil, theanine, tribulus terrestris, turmeric (curcumin), tyrosine, valerian, vitamin A, vitamin B12, vitamin C, vitamin D, vitamin E, vitamin K, whey protein, witch hazel, xanthan gum, xylitol, yohimbe, and zinc.

A microneedle array may include a single substance of interest or it may include two or more substances of interest. In the latter case, the different substances may be provided together within one of the microneedles, or some microneedles in an array of microneedles contain one substance of interest while other microneedles contain another substance of interest.

The API desirably is provided in a stable formulation or composition (i.e., one in which the biologically active material therein essentially retains its physical stability and/or chemical stability and/or biological activity upon storage). Stability can be measured at a selected temperature for a selected period. Trend analysis can be used to estimate an expected shelf life before a material has actually been in storage for that time period.

In embodiments, the substance of interest is provided as a solid that is "dry" or has been "dried" to form the one or more microneedles and becomes solubilized in vivo following insertion of the microneedle into the patient's biological tissue. As used herein, the term "dry" or "dried" refers to a composition from which a substantial portion of any water has been removed to produce a solid phase of the composition. The term does not require the complete absence of moisture (e.g., the API may have a moisture content from about 0.1% by weight and about 25% by weight).

The substance of interest may be included in a formulation with one or more excipients and other additives, as detailed below.

Matrix Material/Excipients

The matrix material forms the bulk of the microneedle and substrate. It typically includes a biocompatible polymeric material, alone or in combination with other materials. In embodiments, the matrix material, at least of the microneedles, is water soluble. In certain preferred embodiments, the matrix material includes one or a combination of polyvinyl alcohol, dextran, carboxymethylcellulose, maltodextrin, sucrose, trehalose, and other sugars. As used herein, the terms "matrix material" and "excipient" are used interchangeably when referring to any excipients that are not volatilized during drying and formation of the microneedles and substrate.

The fluid solution used in the mold filling processes described herein may include any of a variety of excipients. The excipients may consist of those that are widely used in pharmaceutical formulations or ones that are novel. In a preferred embodiment, the excipients are ones in FDA-approved drug products (see the Inactive Ingredient Search for Approved Drug Products at http://www.accessdata.fda.gov/scripts/cder/iig/index.Cfm). None, one, or more than one excipient from the following categories of excipients may be used: stabilizers, buffers, bulking agents or fillers, adjuvants, surfactants, disintegrants, antioxidants, solubilizers, lyo-protectants, antimicrobials, antiadherents, colors, lubricants, viscosity enhancer, glidants, preservatives, materials for prolonging or controlling delivery (e.g., biodegradable polymers, gels, depot forming materials, and others). Also, a single excipient may perform more than one formulation role. For example, a sugar may be used as a stabilizer and a bulking agent or a buffer may be used to both buffer pH and protect the active from oxidation. Some examples of excipients include, but are not limited to lactose, sucrose, glucose, mannitol, sorbitol, trehalose, fructose, galactose, dextrose, xylitol, maltitol, raffinose, dextran, cyclodextrin, collagen, glycine, histidine, calcium carbonate, magnesium stearate, serum albumin (human and/or animal sources), gelatin, chitosan, DNA, hylaruronic acid, polyvinylpyrrolidone, polyvinyl alcohol, polylactic acid (PLA), polyglycolic acid (PGA), polylactive co-glycolic acid (PLGA), polyethylene glycol (PEG, PEG 300, PEG 400, PEG 600, PEG 3350, PEG 4000), cellulose, methylcellulose, carboxymethyl cellulose, sodium carboxymethyl cellulose, hydroxypropyl methylcellulose, acacia, Lecithin, Polysorbate 20, Polysorbate 80, Pluronic F-68, Sorbitantrioleate (span 85), EDTA, hydroxypropyl cellulose, sodium chloride, sodium phosphate, ammonium acetate, potassium phosphate, sodium citrate, sodium hydroxide, sodium carbonate, Tris base-65, Tris acetate, Tris HCl-65, citrate buffer, talc, silica, fats, methyl paraben, propyl paraben, selenium, vitamins (A, E, C, retinyl palmitate, and selenium), amino acids (methionine, cysteine, arginine), citric acid, sodium citrate, benzyl alcohol, chlrorbutanol, cresol, phenol, thimerosal, EDTA, acetone sodium bisulfate, ascorbyl palmitate, ascorbate, castor oil, cottonseed oil, alum, aluminum hydroxide, aluminum phosphate, calcium phosphate hydroxide, paraffin oil, squalene, Quil A, IL-1, IL-2, IL-12, Freund's complete adjuvant, Freund's incomplete adjuvant, killed *Bordetella pertussis, Mycobacterium bovis*, and toxoids. The one or more selected excipients may be selected to improve the stability of the substance of interest during drying and storage of the microneedle devices, as well providing bulk and/or mechanical properties to the microneedle array and/ or serve as an adjuvant to improve the immune response to a vaccine.

Manufacture

The arrays of microneedles may be made by any methods known in the art. For example, the arrays of microneedles may be made using a molding process, which advantageously is highly scalable. The process may include filling a suitable mold with suitable fluidized materials; drying the fluidized material to form the microneedles, the predefined fracture regions if included, and base substrate; and then removing the formed part from the mold. These filling and drying steps may be referred to as "casting" in the art. Preferably the methods for making the microneedles are performed under a minimum ISO 7 (class 10,000) process or an ISO 5 (class 100) process.

In one embodiment, the manufacture of solid, bioerodible microneedles includes filling a negative mold of the one or more microneedles with an aqueous or non-aqueous casting solution of the substance of interest and drying the casting solution to provide the one or more solid microneedles. In other embodiments, other solvent or solventless systems may be used. Non-limiting examples of methods for filling the negative mold include deposition, coating, printing, spraying, and microfilling techniques. The casting solution may be dried or cured at ambient temperature, under refrigeration, or at temperatures above ambient (e.g., 30 to 60° C., or higher) for a period from about 5 seconds to about one week to form the dry solid microneedles. In some embodiments, the dry or cure time is from about 10 seconds to about 24 hours, from about 30 minutes to about 12 hours, from about 10 minutes to about 1 hour, or from about 1 minute to about 30 minutes. In a preferred embodiment, the dry or cure time is from about 10 seconds to about 30 minutes.

Alternatively, the casting solution may be vacuum-filled or filled into the mold using a combination of non-vacuum filling and vacuum-filling. For example, in an embodiment the negative mold comprises a non-porous but gas-permeable material (e.g., PDMS) through which a backside vacuum can be applied. Although the negative mold is solid, it was determined that a sufficient vacuum could be applied through the backside when the molds are formed of such materials. In some embodiments, the backside vacuum may be used alone or in combination with a positive pressure applied on top of the mold for quicker filling. Such embodiments could advantageously reduce the time required and improve the accuracy and completeness when filling the mold with casting solution. For example, the casting solution may be vacuum-filled using a backside vacuum for a period from about 3 minutes to about 6 hours, from about 3 minutes to about 3 hours, from about 3 minutes to about 1 hour, or from about 3 minutes to about 30 minutes.

Although various temperatures and humidity levels can be employed to dry the casting solution, the formulations preferably are dried at temperature from about 1° C. to about 150° C. (e.g., from about 5° C. to about 99° C., from about 15° C. to about 45° C., from about 25° C. to about 45° C., or at about ambient temperature) and about 0 to about 40% relative humidity, e.g., about 0% to about 20% relative humidity.

In some embodiments, it may be desirable to use a multi-step casting process to form the microneedles and substrate. For example, the tips of the microneedles may be partially filled in a first step with a casting solution comprising the substance of interest followed by one or more subsequent fill steps with casting solutions of bulking polymers with or without the same or a different substance of interest. After filling and at least partially drying the microneedles in the negative mold, the adhesive layer and backing layer may be applied to the base substrate prior to removing the microneedles from the mold. In some embodiments, the adhesive layer and/or backing layer are pre-formed prior to application to the base substrate, while in other embodiments the adhesive layer and/or backing layer may be formed directly in-line.

In one embodiment, the multi-step casting process includes (1) a first cast of API in excipient forming the microneedles, (2) a second cast of a frangible material forming a fracture region, and (3) a third cast of a matrix material forming the backing and/or base substrate.

After at least partially drying the microneedles, the microneedles may be removed from the mold. For example, the microneedles may be removed from the mold before fully dry (e.g., when still in a rubbery state), but when strong enough to be peeled, and then dried further once removed from the mold to further solidify/harden the microneedles. Such a technique may be useful when carboxymethylcellulose sodium, polyvinyl alcohol, sugars, and other materials are used as a bulking polymer (matrix material) in the microneedles. In such embodiments, the microneedles may complete drying prior to or after packaging.

The devices and methods described above may be further understood with reference to the following non-limiting examples.

Example 1

A microneedle array was fabricated as follows: A first solution (of 10 wt % sucrose, 1 wt % carboxymethyl cellulose in potassium phosphate buffer) was cast under vacuum into polydimethylsiloxane (PDMS) microneedle molds and dried under ambient conditions for 10 minutes to form the microneedles. Then a second solution (of 10 wt % sucrose, 1 wt % carboxymethyl cellulose in potassium phosphate buffer) was cast under vacuum in the PDMS microneedle molds and dried overnight at 35° C. to form the substrate/base layer. Then an adhesive backing (support layer) (3M 1503 tan single-coated polyethylene medical tape) was applied to the base of microneedle array, forming a microneedle patch. The microneedle array was then removed from mold and packaged with desiccant in a foil pouch.

Example 2

The microneedle array made in Example 1 was applied to excised porcine skin, to insert the microneedles into the skin. Then the patch was pulled laterally (horizontally, parallel to the surface of the skin) while maintaining a downward force to keep the patch secured against the tissue surface. The patch was then pulled away from the skin and imaged. A hydrophilic dye (Gentian violet, 1%) was then applied to the porcine skin at the area of the microneedle insertion. The dye was allowed to sit on the surface of the porcine skin for 30 seconds, and then it was wiped away with an isopropanol wipe. Then, the surface of the porcine skin was imaged and evaluated for staining.

A downward applied force of approximately 10 $lb_f$ was applied to the patch immediately followed by pulling the patch horizontally across the skin. This resulted in separation of the microneedles from the substrate, but it also resulted in surface tears of the stratum corneum/epidermis as evidenced by gentian staining on the treated porcine skin.

A smaller downward force (<5 $lb_f$) was then applied and then patch was horizontally pulled across the skin. This resulted in less tearing of the stratum corneum/epidermis, but also reduced microneedle penetration.

Example 3

Another microneedle array was fabricated as follows: A first solution (of 10 wt % sucrose, 1 wt % carboxymethyl cellulose, and 0.1% sulforhodamine B (red dye) in potassium phosphate buffer) was cast under vacuum into polydimethylsiloxane (PDMS) microneedle molds and dried for 30 minutes at 40° C. to form the microneedles. Then a second fluid (a mixture of a two-part polyurethane high durometer elastomer (60D liquid urethane, Forsch Polymer Corp.) was cast under vacuum into the PDMS microneedle molds and let to cure overnight to form the tapered substrate/base layer. Then an adhesive backing (support layer) (3M 1503 tan single-coated polyethylene medical tape) was applied to the base of microneedle array, forming a microneedle patch. The microneedle array was then removed from mold and packaged with desiccant in a foil pouch.

Example 4

The microneedle array made in Example 3 was applied to excised porcine skin, to insert the microneedles into the skin. Then the patch was pulled laterally (horizontally, parallel to the surface of the skin) while maintaining a downward force to keep the patch secured against the tissue surface. The dye that was incorporated into the microneedles was released into the skin, so secondary staining was not performed. Then, the surface of the porcine skin was imaged and evaluated for staining. The patch was pulled away from the skin and also imaged.

All of the microneedles were separated from the substrate and left embedded in the skin, as evidenced by light micrographs of the remains of the microneedle array and the porcine skin (which showed delivery of the microneedle dye payload). There was minimal tearing of the skin surface.

A comparison of the results of Examples 1-2 and Examples 3-4 showed that the array of Examples 3-4 had a clearly-defined point of separation, which was the interface of the two separate and distinct materials from the first and second castings. The first array is made by two water soluble casting solutions that mix and this did not result in a clear separation/interface. The array of Examples 3-4 also had an interface that was well-defined by two differently sloping walls that intersect to define a clear angle, unlike the array of Examples 1-2, in which the array was parabolic (i.e., radius) at the interface of the two materials from the first and second castings. Thus, the geometry of the interface between the microneedles and the substrate was important to the separation process in this example.

The array of Examples 3-4 also had an elastomeric material, albeit with a high durometer, that allowed for more simple microneedle separation and minimized tearing of the skin during the application of the shear force for separating the microneedles from the substrate/funnels.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A drug delivery device for administering a drug into a skin tissue, the device comprising:
    an array of microneedles which comprise a drug and which extend from a base;
    a system configured to trigger, after the microneedles are inserted at least partially into a skin tissue, a change in rate of release of the drug from the microneedles and into the skin tissue; and
    means for separating tip portions of the microneedles from proximal end portions of the microneedles extending from the base following insertion of the microneedles into the skin tissue, wherein the separation occurs, at an interface of two distinct materials, upon application of a force to the base sufficient to at least partially penetrate the skin tissue with the array of microneedles.

2. The drug delivery device of claim 1, wherein the tip portions of the microneedles are bioerodible.

3. The drug delivery device of claim 1, wherein one of the two distinct materials is an elastomeric material.

4. The drug delivery device of claim 3, wherein the elastomeric material comprises a polyurethane.

5. The drug delivery device of claim 1, further comprising a barrier material that includes (i) a first coating on a first part of the microneedles, the first coating comprising a biodegradable polymer, and (ii) a second coating on a second part of the microneedles, the second coating being soluble in biological fluid, wherein the barrier material is configured such that upon penetration of the microneedles into the skin tissue, the second coating dissolves to permit release of the drug to (a) the dermis while the first coating prevents release of the drug to the epidermis, or (b) the epidermis while the first coating prevents release of the drug to the dermis.

6. A drug delivery device comprising:
    a substrate having a microneedle side and an opposing back side;
    an array of microneedles extending from the microneedle side of the substrate, wherein the microneedles comprise a drug;
    a supporting layer arranged on the opposing back side of the substrate; and
    wherein the microneedles are coated with a barrier so that upon separation of the microneedles following insertion into a tissue surface, the drug is released only from an end portion of the microneedles where the separation occurred.

7. The drug delivery device of claim 6, wherein the microneedles are bioerodible.

8. The drug delivery device of claim 6, wherein the microneedles are configured to be inserted into skin and to separate from the substrate near the dermal-epidermal junction.

9. A drug delivery device comprising:
    a substrate having a microneedle side and an opposing back side; and
    an array of microneedles extending from the microneedle side of the substrate,
    wherein the microneedles are formed by a molding process which comprises at least two castings, whereby each of the microneedles comprises (i) a tip portion comprising a first material which comprises a drug, and (ii) a proximal end portion comprising a second material, wherein the first and second materials are different in composition form one another and have an interface forming a predefined region configured to effect separation of the tip portion from the proximal end portion upon application of a force to the substrate sufficient to at least partially penetrate into a patient's skin with the array of microneedle.

10. The drug delivery device of claim 9, wherein the first material comprises a bioerodible matrix material in which the drug is dispersed.

11. The drug delivery device of claim 10, wherein the bioerodible matrix material comprises a water soluble matrix material.

12. The drug delivery device of claim 10, wherein the bioerodible matrix material comprises one or more of polyvinyl alcohol, dextran, carboxymethylcellulose, maltodextrin, sucrose, trehalose, and other sugars.

13. The drug delivery device of claim 10, wherein the bioerodible matrix material comprises a biodegradable polymer.

14. The drug delivery device of claim 13, wherein the biodegradable polymer comprises polylactic acid (PLA), polyglycolic acid (PGA), or poly(lactic-co-glycolic) acid (PLGA).

15. The drug delivery device of claim 9, wherein the second material comprises a biocompatible polymeric material.

16. The drug delivery device of claim 15, wherein the biocompatible polymeric material comprises an elastomer.

17. The drug delivery device of claim 9, wherein the second material does not comprise the drug.

18. The drug delivery device of claim 9, wherein the proximal end portion of the microneedles comprises a funnel portion.

19. The drug delivery device of claim 9, wherein the interface is well-defined by two differently sloping walls that intersect.

20. The drug delivery device of claim 9, wherein the predefined region is a predefined fracture region.

21. The drug delivery device of claim 9, wherein the drug comprises a vaccine.

22. The drug delivery device of claim 9, wherein the drug comprises a protein, peptide, or fragment thereof.

23. A drug delivery device comprising:
an array of microneedles extending from a base substrate, wherein the microneedles each comprise a tip portion comprising a first material in which a drug is dispersed, and a proximal end portion comprising a second material which is different in composition from the first material,
wherein the first and second materials have an interface configured to effect separation of the tip portions from the proximal end portions, wherein the separation of the tip portions from the proximal end portions occurs upon application of an input force applied by a user to the drug delivery device to at least partially penetrate a patient's skin with the microneedles.

24. The drug delivery device of claim 23, wherein the microneedles have substantially straight, tapered sidewalls.

25. The drug delivery device of claim 23, wherein the drug comprises a vaccine.

26. The drug delivery device of claim 23, wherein the drug comprises a protein, peptide, or fragment thereof.

27. The drug delivery device of claim 23, wherein the first material is a water soluble matrix material.

28. The drug delivery device of claim 23, wherein the first material comprises a biodegradable polymer.

* * * * *